US012131393B2

(12) United States Patent
Stewart et al.

(10) Patent No.: US 12,131,393 B2
(45) Date of Patent: Oct. 29, 2024

(54) PLATFORM FOR REAL-TIME IDENTIFICATION AND RESOLUTION OF SPATIAL PRODUCTION ANOMALIES IN AGRICULTURE

(71) Applicant: Ecoation Innovative Solutions Inc., North Vancouver (CA)

(72) Inventors: Gregory E. Stewart, North Vancouver (CA); Adrian M. Fuxman, North Vancouver (CA); Lino E. Coria Mendoza, Port Moody (CA); Saber Miresmailli, North Vancouver (CA); Allison Marie Christensen, Vancouver (CA)

(73) Assignee: Ecoation Innovative Solutions Inc., North Vancouver (CA)

( * ) Notice: Subject to any disclaimer, the term of this patent is extended or adjusted under 35 U.S.C. 154(b) by 933 days.

(21) Appl. No.: 17/062,381

(22) Filed: Oct. 2, 2020

(65) Prior Publication Data
US 2022/0107297 A1    Apr. 7, 2022

(51) Int. Cl.
*G06Q 50/02*        (2024.01)
*G06Q 10/0637*      (2023.01)
(Continued)

(52) U.S. Cl.
CPC ......... *G06Q 50/02* (2013.01); *G06Q 10/0637* (2013.01); *G01N 33/0098* (2013.01); *G05B 15/02* (2013.01); *G06N 20/00* (2019.01)

(58) Field of Classification Search
CPC .... G01N 33/0098; G05B 15/02; G06N 20/00; G06Q 10/0637; G06Q 50/02
See application file for complete search history.

(56) References Cited

U.S. PATENT DOCUMENTS

| 4,755,942 A | 7/1988 | Gardner et al. |
| 4,876,647 A | 10/1989 | Gardner et al. |

(Continued)

FOREIGN PATENT DOCUMENTS

| CA | 2760817 A1 | 11/2010 |
| CA | 2881675 A1 | 2/2014 |

(Continued)

OTHER PUBLICATIONS

Bendig et al., "Combining UAV-based plant height from crop surface models, visible, and near infrared vegetation indices for biomass monitoring in barley," International Journal of Applied Earth Observation and Geoinformation, Mar. 2015, 9 pages.

(Continued)

*Primary Examiner* — Charles Guiliano

(57) ABSTRACT

A method includes obtaining data measurements associated with plants in at least one growing area. The data measurements are associated with one or more characteristics of the plants and one or more characteristics of the at least one growing area. The method also includes processing at least some of the data measurements to identify one or more anomalous plant production issues associated with the plants. At least one anomalous plant production issue is associated with uneven production by the plants in at least part of the at least one growing area. The method further includes generating at least one visualization presenting at least some of the data measurements or processed versions of at least some of the data measurements in a spatial manner that corresponds to the at least one growing area. The at least one visualization identifies information associated with the one or more anomalous plant production issues.

53 Claims, 10 Drawing Sheets

(51) Int. Cl.
   *G01N 33/00* (2006.01)
   *G05B 15/02* (2006.01)
   *G06N 20/00* (2019.01)

(56) References Cited

U.S. PATENT DOCUMENTS

| | | | |
|---|---|---|---|
| 5,130,545 | A | 7/1992 | Lussier |
| 5,764,819 | A | 6/1998 | Orr et al. |
| 5,839,106 | A | 11/1998 | Bellegarda |
| 6,397,162 | B1 | 5/2002 | Ton |
| 6,573,512 | B1 | 6/2003 | Lucia et al. |
| 6,657,117 | B2 | 12/2003 | Weare et al. |
| 6,701,665 | B1 | 3/2004 | Ton et al. |
| 7,112,806 | B2 | 9/2006 | Lussier |
| 7,412,330 | B2 | 8/2008 | Spicer et al. |
| 7,487,925 | B2 | 2/2009 | Skinner |
| 7,617,057 | B2 | 11/2009 | May et al. |
| 7,715,013 | B2 | 5/2010 | Glaser et al. |
| 7,987,632 | B2 | 8/2011 | May et al. |
| 8,028,470 | B2 | 10/2011 | Anderson |
| 8,056,284 | B2 | 11/2011 | He |
| 8,061,080 | B2 | 11/2011 | Loebl et al. |
| 8,249,308 | B2 | 8/2012 | Lussier |
| 8,437,498 | B2 | 5/2013 | Malsam |
| 8,437,879 | B2 | 5/2013 | Anderson |
| 8,476,603 | B2 | 7/2013 | Moise et al. |
| 8,504,234 | B2 | 8/2013 | Anderson |
| 8,836,504 | B2 | 9/2014 | Kohler et al. |
| 9,107,354 | B2 | 8/2015 | Martin et al. |
| D737,840 | S | 9/2015 | Omiya |
| 9,532,411 | B2 | 12/2016 | Conrad et al. |
| 9,576,786 | B2 | 2/2017 | Greenberg et al. |
| 9,939,132 | B2 | 4/2018 | Greenberg et al. |
| 9,992,991 | B2 | 6/2018 | Cink et al. |
| 10,021,837 | B2 | 7/2018 | Greenberg et al. |
| 10,031,117 | B2 | 7/2018 | Koutsky et al. |
| 10,241,097 | B2 | 3/2019 | Miresmailli et al. |
| 10,339,380 | B2 | 7/2019 | Greenberg et al. |
| 10,349,584 | B2 | 7/2019 | Itzhaky et al. |
| 10,627,785 | B2 | 4/2020 | King et al. |
| 10,635,274 | B2 | 4/2020 | Greenberg et al. |
| 10,701,852 | B2 | 7/2020 | Calleija et al. |
| 10,791,037 | B2 | 9/2020 | Greenberg et al. |
| 10,871,480 | B2 | 12/2020 | Miresmailli et al. |
| 10,929,664 | B2 | 2/2021 | King |
| 10,949,974 | B2 | 3/2021 | King et al. |
| 10,966,377 | B2 | 4/2021 | Xu |
| 11,003,456 | B2 | 5/2021 | King |
| 11,062,516 | B2 | 7/2021 | Greenberg et al. |
| 2002/0167587 | A1 | 11/2002 | Ogasawara |
| 2002/0170229 | A1 | 11/2002 | Ton et al. |
| 2003/0229497 | A1 | 12/2003 | Wilson et al. |
| 2004/0241635 | A1 | 12/2004 | Buckley |
| 2006/0137041 | A1 | 6/2006 | Masle et al. |
| 2007/0289207 | A1 | 12/2007 | May et al. |
| 2011/0101239 | A1 | 5/2011 | Woodhouse et al. |
| 2011/0261355 | A1 | 10/2011 | Hannel et al. |
| 2012/0046837 | A1 | 2/2012 | Anderson |
| 2012/0101861 | A1 | 4/2012 | Lindores |
| 2012/0109387 | A1 | 5/2012 | Martin et al. |
| 2012/0114187 | A1 | 5/2012 | Duarte |
| 2012/0150355 | A1 | 6/2012 | Anderson |
| 2014/0035752 | A1 | 2/2014 | Johnson |
| 2014/0059722 | A1 | 2/2014 | Krichevsky |
| 2014/0064568 | A1 | 3/2014 | Moon et al. |
| 2014/0152669 | A1 | 6/2014 | Omiya |
| 2014/0180549 | A1 | 6/2014 | Siemens et al. |
| 2014/0222374 | A1 | 8/2014 | Lock et al. |
| 2014/0358486 | A1 | 12/2014 | Osborne |
| 2015/0027040 | A1 | 1/2015 | Redden |
| 2015/0199846 | A1* | 7/2015 | Sanderson ........... G06T 11/206 703/11 |
| 2015/0278603 | A1 | 10/2015 | Boriah et al. |
| 2016/0308954 | A1 | 10/2016 | Wilbur et al. |
| 2017/0030877 | A1 | 2/2017 | Miresmailli et al. |
| 2017/0032258 | A1 | 2/2017 | Miresmailli et al. |
| 2017/0176595 | A1 | 6/2017 | McPeek |
| 2017/0332544 | A1 | 11/2017 | Conrad et al. |
| 2017/0359943 | A1 | 12/2017 | Calleija et al. |
| 2018/0082362 | A1 | 3/2018 | Greenberg et al. |
| 2018/0082375 | A1 | 3/2018 | Greenberg et al. |
| 2018/0146626 | A1 | 5/2018 | Xu |
| 2018/0330435 | A1 | 11/2018 | Garg |
| 2019/0050948 | A1 | 2/2019 | Perry et al. |
| 2019/0059202 | A1 | 2/2019 | Lorek |
| 2019/0098842 | A1 | 4/2019 | Barber, III et al. |
| 2019/0170718 | A1 | 6/2019 | Miresmailli et al. |
| 2019/0303713 | A1 | 10/2019 | Kumar et al. |
| 2020/0019777 | A1* | 1/2020 | Gurzoni, Jr. ......... G06V 10/803 |
| 2020/0193589 | A1* | 6/2020 | Peshlov ............... G06V 10/955 |
| 2020/0202127 | A1 | 6/2020 | Chen et al. |
| 2020/0241579 | A1 | 7/2020 | Ben-Ner et al. |
| 2020/0265227 | A1* | 8/2020 | Chen ..................... G06V 10/22 |
| 2020/0380616 | A1 | 12/2020 | King et al. |
| 2021/0298244 | A1 | 9/2021 | King et al. |
| 2021/0302973 | A1 | 9/2021 | King et al. |
| 2021/0304216 | A1 | 9/2021 | King et al. |
| 2021/0304326 | A1 | 9/2021 | Greenberg et al. |

FOREIGN PATENT DOCUMENTS

| | | | |
|---|---|---|---|
| CA | 2956205 | A1 | 12/2015 |
| CA | 2987319 | A1 | 12/2016 |
| CA | 2990438 | A1 | 1/2017 |
| CA | 3044072 | A1 | 5/2018 |
| CA | 3098485 | A1 | 11/2019 |
| CN | 105069292 | A | 11/2015 |
| CN | 105095660 | A | 11/2015 |
| CN | 105631218 | A | 6/2016 |
| DE | 10148747 | A1 | 4/2003 |
| EP | 3491613 | A1 | 6/2019 |
| EP | 3850460 | A1 | 7/2021 |
| JP | 6963102 | B2 | 11/2021 |
| WO | 2009141465 | A1 | 11/2009 |
| WO | 2016110832 | A1 | 7/2016 |
| WO | 2018057799 | A1 | 3/2018 |
| WO | 2018203337 | A1 | 11/2018 |
| WO | 2019144231 | A1 | 8/2019 |
| WO | 2020132674 | A1 | 6/2020 |

OTHER PUBLICATIONS

Jansen et al., "Induced plant volatiles allow sensitive monitoring of plant health status in greenhouses," Plant Signaling & Behavior, 2009, pp. 824-829.

Koppert Biological Systems, "Airbug," Product Specification, Apr. 2020, 3 pages.

Koppert Biological Systems, "Biological pest management to ensure healthy crops," Product List, Dec. 2016, 1 page.

Mandow et al., "The Autonomous Mobile Robot AURORA for Greenhouse Operation," IEEE Robotics and Automation Magazine, Dec. 1996, 11 pages.

Nicolai et al., "Nondestructive measurement of fruit and vegetable quality by means of NIR spectroscopy: A review," Science Direct, Postharvest Biology and Technology, 2007, pp. 99-118.

Ruiz-Altisent et al., "Sensors for product characterization and quality of specialty crops—A review," Computers and Electronics in Agriculture, 2010, pp. 176-194.

Sankaran et al., "A review of advanced techniques for detecting plant diseases," Computer and Electronics in Agriculture, vol. 72, Jun. 2010, 13 pages.

Story et al., "Automated Machine Vision Guided Plant Monitoring System for Greenhouse Crop Diagnostics," Acta Hortic, 2014, pp. 636-641 (abstract only).

Ton et al., "Phytomonitoring: A Bridge from Sensors to Information Technology for Greenhouse Control," Phytech Ltd., 2003, pp. 639-644.

Office Action dated Jul. 1, 2020 in connection with U.S. Appl. No. 16/268,744, 20 pages.

Office Action dated Mar. 11, 2020 in connection with U.S. Appl. No. 15/219,328, 21 pages.

(56) References Cited

OTHER PUBLICATIONS

Office Action dated Sep. 18, 2020 in connection with U.S. Appl. No. 15/219,328, 24 pages.
International Search Report and Written Opinion of the International Searching Authority in connection with International Patent Application No. PCT/CA2020/051099 dated Nov. 6, 2020, 11 pages.
Fuxman et al., "Real-Time Projections and Estimated Distributions of Agricultural Pests, Diseases, and Biocontrol Agents," U.S. Appl. No. 16/883,354, filed May 26, 2020, 52 pages.
Miresmailli, "Mobile Platform for Crop Monitoring and Treatment," U.S. Appl. No. 16/990,212, filed Aug. 11, 2020, 42 pages.
Fuxman et al., "Reduction of Time of Day Variations in Plant-Related Data Measurements," U.S. Appl. No. 17/062,397, filed Oct. 2, 2020, 72 pages.
Stewart et al., "System and Method for Testing Plant Genotype and Phenotype Expressions Under Varying Growing and Environmental Conditions," U.S. Appl. No. 17/062,407, filed Oct. 2, 2020, 75 pages.
Non-Final Office Action dated Mar. 28, 2022 in connection with U.S. Appl. No. 17/062,397, 31 pages.
Final Office Action dated May 27, 2022 in connection with U.S. Appl. No. 17/062,397, 29 pages.
Office Action dated Dec. 12, 2022 in connection with U.S. Appl. No. 17/062,397, 33 pages.
Office Action dated Jan. 11, 2023 in connection with U.S. Appl. No. 17/062,407, 47 pages.
International Search Report and Written Opinion of the International Searching Authority dated Oct. 14, 2021 in connection with International Patent Application No. PCT/CA2021/050958, 8 pages.
International Search Report and Written Opinion of the International Searching Authority dated Oct. 12, 2021 in connection with International Patent Application No. PCT/CA2021/050959, 9 pages.
International Search Report and Written Opinion of the International Searching Authority dated Oct. 12, 2021 in connection with International Patent Application No. PCT/CA2021/050960, 20 pages.
Supplementary European Search Report dated Sep. 9, 2024 in connection with the European Patent Application No. 21873755.9, 10 pages.

\* cited by examiner

PLATFORM FOR REAL-TIME IDENTIFICATION AND RESOLUTION OF SPATIAL PRODUCTION ANOMALIES IN AGRICULTURE

TECHNICAL FIELD

This disclosure is generally directed to plant monitoring and assessment. More specifically, this disclosure is directed to a platform for real-time identification and resolution of spatial production anomalies in agriculture.

BACKGROUND

When plants are grown on a large scale, such as in protected cultivation (like a greenhouse) or outdoors, both the plants and their growers face various challenges. For example, production greenhouses can involve very complex and geographically large operations with varying environmental conditions. The management of growing operations in production greenhouses can be very difficult and time consuming, and conventional approaches for managing the growing operations in greenhouses can suffer from a number of shortcomings. The same problems and difficulties can occur in other large growing areas, such as in open outdoor fields.

SUMMARY

This disclosure relates to a platform for real-time identification and resolution of spatial production anomalies in agriculture.

In a first embodiment, an apparatus includes at least one processor configured to obtain data measurements associated with plants in at least one growing area. The data measurements are associated with one or more characteristics of the plants and one or more characteristics of the at least one growing area. The at least one processor is also configured to process at least some of the data measurements to identify one or more anomalous plant production issues associated with the plants. At least one of the one or more anomalous plant production issues is associated with uneven production by the plants in at least part of the at least one growing area. The at least one processor is further configured to generate at least one visualization presenting at least some of the data measurements or processed versions of at least some of the data measurements in a spatial manner that corresponds to the at least one growing area. The at least one visualization identifies information associated with the one or more anomalous plant production issues.

In a second embodiment, a non-transitory computer readable medium contains instructions that when executed cause at least one processor to obtain data measurements associated with plants in at least one growing area. The data measurements are associated with one or more characteristics of the plants and one or more characteristics of the at least one growing area. The medium also contains instructions that when executed cause the at least one processor to process at least some of the data measurements to identify one or more anomalous plant production issues associated with the plants. At least one of the one or more anomalous plant production issues is associated with uneven production by the plants in at least part of the at least one growing area. The medium further contains instructions that when executed cause the at least one processor to generate at least one visualization presenting at least some of the data measurements or processed versions of at least some of the data measurements in a spatial manner that corresponds to the at least one growing area. The at least one visualization identifies information associated with the one or more anomalous plant production issues.

In a third embodiment, a method includes obtaining data measurements associated with plants in at least one growing area. The data measurements are associated with one or more characteristics of the plants and one or more characteristics of the at least one growing area. The method also includes processing at least some of the data measurements to identify one or more anomalous plant production issues associated with the plants. At least one of the one or more anomalous plant production issues is associated with uneven production by the plants in at least part of the at least one growing area. The method further includes generating at least one visualization presenting at least some of the data measurements or processed versions of at least some of the data measurements in a spatial manner that corresponds to the at least one growing area. The at least one visualization identifies information associated with the one or more anomalous plant production issues.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

Figure 1:
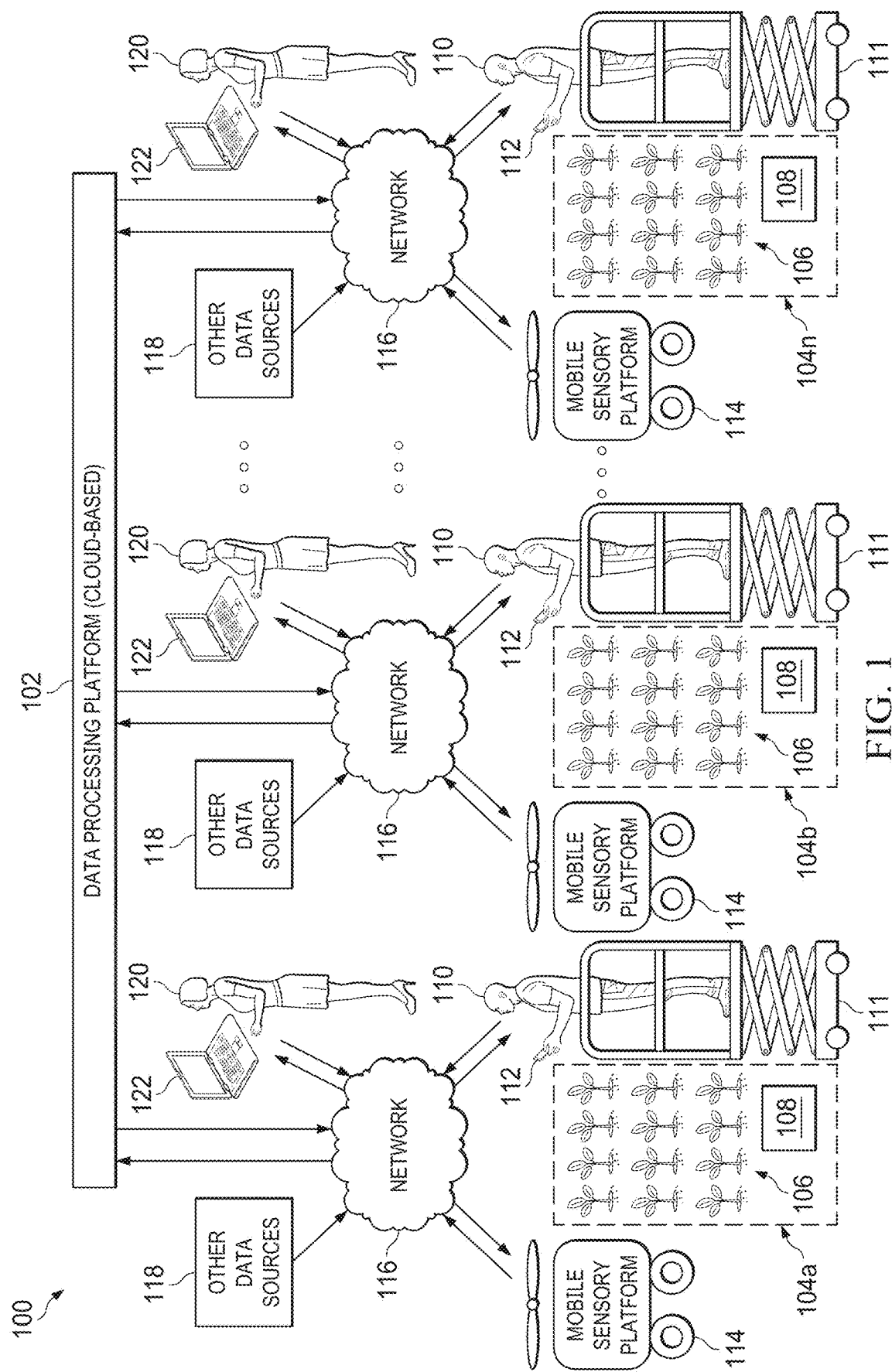
FIG. 1 illustrates an example system for collecting and processing plant-related data according to this disclosure.

FIGS. 1 through 10, described below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device or system.

As noted above, when plants are grown on a large scale, such as in protected cultivation (like a greenhouse) or outdoors, both the plants and their growers face various challenges. For example, production greenhouses can involve very complex and geographically large operations with varying environmental conditions. The management of growing operations in production greenhouses can be very difficult and time consuming, and conventional approaches for managing the growing operations in greenhouses can suffer from a number of shortcomings. The same problems and difficulties can occur in other large growing areas, such as in open outdoor fields.

As one example issue, uneven production across a greenhouse or other growing area can lead to significant economic losses. Unfortunately, identifying areas of low production and understanding the root cause(s) of low production may require measuring, collecting, visualizing, and analyzing a wide variety of data from across the greenhouse or other growing area. This is typically not possible today because (i) area-wide measurements are not available, (ii) measurements that are available do not have enough spatial granularity, or (iii) data is not available in a way that can be used to understand or calculate how multiple variables impact production together. As a result, opportunities to detect, identify, and correct causes of low production are routinely missed.

In one aspect, this disclosure provides a platform for real-time identification and resolution of spatial production anomalies in agriculture. As described in more detail below, the platform supports the collection of measurement data and other plant-related data. The collected data may include, but is not limited to, plant production data, physical plant data (such as phenotypical and genotypical data), climate data, pest and disease data, crop work data, and crop treatment data. The platform also supports various analyses and visualizations that allow growers or other personnel to identify specific plants in or zones of at least one growing area that are experiencing plant production issues or phenotypical/genotypical diversions and to understand one or more potential causes of the plant production issues or phenotypical/genotypical diversions. A plant production issue or phenotypical/genotypical diversion may involve under-production (such as when a plant or zone is under-producing relative to other plants or zones), in which case the growers or other personnel may wish to understand the underlying cause(s) and identify at least one appropriate remedy to increase production. A plant production issue or phenotypical/genotypical diversion may alternatively involve over-production (such as when a plant or zone is over-producing relative to other plants or zones), in which case the growers or other personnel may wish to understand the underlying cause(s) and possibly replicate conditions for other plants or zones. Note that this may occur for plants being grown in any suitable growing area or areas, such as in one or more greenhouses, open fields, or other protected, partially protected, or unprotected growing areas.

Plant production data generally refers to data identifying one or more physical characteristics associated with actual production by plants being monitored in at least one greenhouse or other growing area. Fruits, vegetables, ornamental flowers, or other production produced by plants may be generally referred to as "production items," and any characteristics of the production items may be generally referred to as "production characteristics." Examples of plant production data may include a number of production items currently growing on plants; a number of production items on the ground or removed from plants; one or more colors of production items; a taste of production items; a shine of production items; a firmness of production items; a shape of production items; a smell of production items; internodal distance between production item-bearing branches of plants; a leaf area index of leaves of plants; a size of foliage of plants; a color of foliage of plants; a thickness of foliage of plants; a distribution of flowers of plants; a number of flowers of plants; total harvest (such as weight per row of plants) for a particular time period; and/or yield assessment (such as sizes and weights of fruits, vegetables, ornamental flowers, or other harvested production). In some cases, the colors of fruits, vegetables, ornamental flowers, or other production items may be used as indicators of ripeness or ready states of the production. These example types of plant production data are for illustration only.

Physical plant data generally refers to data identifying one or more physical characteristics associated with plants being monitored in at least one greenhouse or other growing area. Examples of physical plant data may include heights of plants; widths of plants; visual data (such as one or more colors) associated with plants' leaves, stems, or other portions; spectrographic data associated with plants' leaves, stems, or other portions; a number of plant stems growing in each of various locations; a spacing of plant stems growing in each of various locations; a density of plant stems at each of various locations; thicknesses of plant stems; an amount of water provided to each plant; one or more nutrients provided to each plant; the genotype of each plant; the smell of each plant associated with its chemical composition and nutritional value and taste; and/or the color of fruits and foliage associated with stress levels and health of the plants. These example types of physical plant data are for illustration only.

Climate data generally refers to data identifying climatic conditions of plants being monitored in at least one greenhouse or other growing area. Examples of climate data may include temperature; absolute or relative humidity; wind/air speed; carbon dioxide level; oxygen level; nitrogen dioxide level; ethylene level; amount of natural or artificial light; flux of light from the top of the canopy to the bottom of the canopy for the plants; spectral composition of light from the top of the canopy to the bottom of the canopy for the plants; vapor-pressure deficit (VPD); dew point; and/or thermal imaging. Since climatic conditions can often vary even within the same greenhouse, field, or other growing area, at least some of the climate data can be specific to each individual plant being monitored. These example types of climate data are for illustration only.

Pest and disease data generally refers to data identifying pests or diseases that might be affecting plants being monitored in at least one greenhouse or other growing area. Pests refer to animals or plants that are detrimental to the growth or well-being of plants being monitored. Pests can include ectoparasites such as certain types of insects, mites, and vertebrates. Specific examples of pests can include whiteflies, aphids, thrips, spider mites, russet mites, mealybugs, caterpillars, sciarid flies, shore flies, leaf miners, vine weevils, red palm weevils, white grubs, and loopers. Diseases refer to pathogens that are detrimental to the growth or well-being of plants being monitored. Specific examples of diseases may include certain types of bacteria, viruses, fungi like powdery mildew, oomycetes, protozoa, and nematodes. Examples of pest and disease data may include a number or quantity of each pest or disease at each of various locations; a current pressure of each pest or disease at each of various locations; historical data regarding pests and diseases; and/or human, machine, or plant movements that may represent vectors for spreading pests and diseases. These example types of pest and disease data are for illustration only.

Crop work data generally refers to data identifying one or more characteristics associated with how humans or machines manipulate, modify, and (possibly) damage plants being monitored in at least one greenhouse or other growing area. Examples of crop work data may include a number of plants remaining after plant work has been completed; a number of stems remaining after plant work has been completed; a spacing of plants or stems after plant work has been completed; a number of broken plant heads present after plant work has been completed; whether deleafing was performed during plant work; and/or a number of leaves or other portions of plants on the ground or removed as a result of plant work. These example types of crop work data are for illustration only.

Crop treatment data generally refers to data identifying one or more treatments, interventions, or biocontrol agents (collectively referred to as "treatments") that are used to help combat pests, diseases, or other problems with plants being monitored in at least one greenhouse or other growing area. Treatments can include the application or use of beneficial organisms, insecticidal soaps (such as one containing a potassium salt of fatty acids), fertilizers, or chemical insecticides, herbicides, or other chemical treatments. Beneficial organisms generally include living organisms that are beneficial to the growth or well-being of plants being monitored, such as organisms that attack or reduce pests or diseases. Specific examples of beneficial organisms may include certain types of parasitic wasps, predatory mites, beetles (such as ladybugs and ladybirds), fungi, and nematodes. Examples of crop treatment data may include an identification of the treatment(s) applied, a quantity of each treatment applied, and a date/time when each treatment was applied. These example types of crop treatment data are for illustration only.

Among other things, the platform enhances the ability of growers or other personnel to take appropriate actions in response to identified anomalies. The appropriate actions may include treating one or more plants or zones in a greenhouse or other growing area with one or more treatments to help combat pests, diseases, or other problems in order to try and resolve under-production issues. The appropriate actions may also include training (or retraining) personnel on how crop work should be performed so that the personnel are performing the crop work more effectively or with less damage to the plants. The appropriate actions may further include attempting to replicate climatic conditions or other conditions for over-producing plants or zones with other plants or zones of a greenhouse or other growing area. In some cases, the platform may identify one or more recommended courses of action associated with each identified plant production issue and may optionally initiate one or more recommended courses of action (with or without user input). Note that the examples provided above are merely for illustration only and that other actions may occur in response to identified anomalies.

As another example issue, greenhouses and other growing areas are often inspected by human or robotic scouts. The scouts can record information about plants being grown, such as observed physical characteristics of the plants and any observed pests, diseases, or other problems affecting the plants. The scouts can also carry and use various sensors for capturing climate or other sensor measurements associated with the plants. Whether human or robotic scouts are used, it is often the case that plants are not inspected very often. For example, plants are typically arranged in rows in a greenhouse, field, or other growing area, and it is common for each row of plants to be inspected by a scout at a rather lengthy interval (such as once every two to five weeks). Inspections might occur more frequently, but typically only in those areas where problems are known or suspected. Regardless of the inspection frequency, it is extremely common for plants to be inspected at different times of day throughout a growing season. Some measurements, such as temperature or gas levels (like carbon dioxide, oxygen, or nitrogen dioxide levels), can vary depending on the time of day that the measurements are captured.

In another aspect, this disclosure provides techniques for processing and normalizing sensor measurements that can suffer from "time of day" variations. As described in more detail below, the platform mentioned above or another device or system may aggregate sensor measurements and develop at least one baseline that shows how one or more types of sensor measurements vary by time of day. In some embodiments, this can be done for each specific greenhouse, field, or growing area. The at least one baseline may then be used to normalize or otherwise process sensor measurements in order to at least partially remove the effects of the time of day from the sensor measurements. This allows more accurate operations to occur using the sensor measurements.

As still another example issue, the "genotype" of a plant seed, cutting, or tissue culture material is related to the specific genes of a plant that are carried in the seed, cutting, or tissue culture material. The "phenotype" of a plant refers to the characteristics of the plant that are expressed physically when the plant is actually growing. The phenotype of a plant is based on its genotype and its growing and environmental conditions, such as its climate, nutrients, pests, diseases, treatments, and crop work. Plant genotypes are often bred or designed to fulfill a certain group of genotype and phenotype traits, such as shape, color, taste, nutritional level, size, and yield. In order for these desirable traits to flourish, their associated genes must be expressed as the plants are growing. However, biotic and abiotic stressors can emerge at various times during growth of the plants. If these stressors are not treated in time, they can divert the plants from their genetically-designed pathway. Some stressors are known to silence genes and stop expression altogether, while other stressors can cause mutations and modify both the purity of the genotype and various phenotypical features of the plants.

Producers often need prolonged periods of time in order to test seeds, cuttings, or tissue culture materials with new genotypes and phenotypes. This is because the producers typically need to grow plants under various growing and environmental conditions over multiple growing seasons. This allows the producers to identify the growing and environmental conditions that typically result in the desired phenotype(s) for the plants. Producers often use this information to provide agronomic advice to growers or to provide performance guarantees for their seeds, cuttings, or tissue culture materials.

In yet another aspect, this disclosure provides techniques for collecting and analyzing data related to plants with at least one genotype being grown under various growing and environmental conditions, such as in different greenhouses, fields, or other growing areas (or portions thereof). As described in more detail below, the platform mentioned above or another device or system may aggregate measurement data associated with plants being grown under various growing and environmental conditions in order to identify the conditions that result in desired plant characteristics being expressed. The identified conditions may be used to make recommendations to growers on how to best grow plants from seeds, cuttings, or tissue culture materials or to provide production guarantees to growers. Since improved or optimal growing and environmental conditions can be identified based on a large amount of collected data associated with a large number of plants growing in different growing areas, this can be accomplished in significantly shorter times. As a particular example, this may allow a producer to test a new plant genotype or phenotype and identify its optimal growing and environmental conditions within one to two years, rather than five years or more (which is often the case now).

Note that while the three aspects mentioned above may be described below as being implemented using the same device or system, there is no requirement that these three aspects be implemented or used together or supported by a common device or system. A device or system may, for example, implement a platform for real-time identification and resolution of spatial production anomalies with or without time of day corrections and with or without the identification of optimal growing and environmental conditions. Similarly, time of day corrections and the identification of optimal growing and environmental conditions may or may not be used together in a device or system.

FIG. 1 illustrates an example system 100 for collecting and processing plant-related data according to this disclosure. As shown in FIG. 1, the system 100 includes at least one data processing platform 102, which may be used in conjunction with one or more growing areas 104a-104n. The data processing platform 102 collects and processes data associated with various plants 106 being grown in the one or more growing areas 104a-104n. The plants 106 represent any suitable plants being grown and whose condition is monitored and assessed, and the plants 106 may be used for any suitable purposes. For example, the plants 106 may represent crops that provide food for people or animals, crops that provide material for industrial or medicinal purposes, or flowers or other ornamental plants. In general, the system 100 may be used to monitor and assess any suitable type(s) of plant(s) 106, including a single type of plant 106 or multiple types of plants 106. The system 100 may also be used to monitor and assess any suitable number of plants 106.

Each growing area 104a-104n represents any suitable space in which plants 106 can be grown, monitored, and assessed. For example, in some embodiments, each growing area 104a-104n may represent a greenhouse or other protected cultivation area or a portion thereof. Protected cultivation technology is generally used to provide favorable climatic conditions for one or more specific types of plants 106, which can vary based on the specific plants 106 being grown. These favorable climatic conditions can reduce stress levels on the plants 106 and help increase production yields obtained from the plants 106. In other embodiments, each growing area 104a-104n may represent an open field or other outdoor or unprotected area or a portion thereof. In general, the system 100 may be used to monitor and assess plants 106 in any suitable type(s) of growing area(s) 104a-104n, including a single type of growing area 104a-104n or multiple types of growing areas 104a-104n. The system 100 may also be used to monitor and assess plants 106 in any suitable number of growing areas 104a-104n.

Each growing area 104a-104n may optionally include one or more types of equipment 108 used to help facilitate growth of the plants 106. For example, each growing area 104a-104n may include irrigation equipment configured to provide water to the plants 106 and, if necessary, drainage equipment configured to handle water that is not retained by the plants 106 or their associated containers (if any). Each growing area 104a-104n may also include nutrition equipment configured to provide nutritional materials to the plants 106. At least part of the nutrition equipment might be integrated into or with the irrigation equipment so that at least some of the nutritional materials can be provided to the plants 106 via the water that is provided to the plants 106. Each growing area 104a-104n may further include lighting equipment configured to provide artificial lighting or to control natural lighting provided to the plants 106. Each growing area 104a-104n may also include temperature equipment configured to create a desired temperature or temperature range around the plants 106. Each growing area 104a-104n may further include humidity equipment configured to create a desired humidity or humidity range around the plants 106. Each growing area 104a-104n may also include carbon dioxide ($CO_2$) equipment configured to create a desired $CO_2$ level or $CO_2$ range around the plants 106. In addition, each growing area 104a-104n may include pruning, spraying, and/or harvesting equipment used to physically prune the plants 106, spray insecticide or other materials onto the plants 106, and/or harvest the plants 106 or portions thereof. In general, the system 100 may use any suitable type(s) of equipment 108 in each growing area 104a-104n to perform any desired operation(s) involving the plants 106. Note that the specific equipment 108 used here can vary based on a number of factors, such as based on the specific types of plants 106 and whether the plants 106 are grown indoors or outdoors. Also note that different growing areas 104a-104n can include the same type(s) of equipment 108 or different types of equipment 108.

In many cases, the plants 106 in the one or more growing areas 104a-104n are arranged in a specified pattern. For example, the plants 106 in each growing area 104a-104n may typically be arranged in long rows of plants 106, where the rows are spaced apart from one another. This helps to provide space for people or objects to move between the plants 106 and to ensure that each plant 106 receives adequate lighting, air flow, moisture, etc. If used in a greenhouse, for example, each plant 106 or group of plants 106 may be placed into a suitable container, and the containers may be arranged in rows in order to facilitate easy movement of the plants 106 as needed or desired. In some instances, the containers themselves may be raised off the ground using suitable holders, which may help to facilitate improved drainage of the containers or to reduce the ability of pests to easily reach the containers. Greenhouses or other structures also often include vertical posts (possibly at generally regular intervals) that are used to provide structural support, and the posts may often be numbered or otherwise identified in order to identify specific locations in the greenhouses or other structures. For instance, plant positions or locations may be identified based on the plants' row numbers and post numbers.

One or more human scouts 110 are often employed to walk or ride around the one or more growing areas 104a-104n and to manually inspect the plants 106. For example, each human scout 110 may visually inspect various plants 106 in order to identify any fruits, vegetables, ornamental flowers, or other production items (or characteristics thereof) currently growing on the plants 106. Each human scout 110 may also visually inspect various plants 106 in order to identify any visible signs of pests, diseases, over- or under-watering, malnutrition, or other problems (or characteristics thereof) associated with the plants 106. As another example, each human scout 110 may visually inspect various plants 106 in order to identify any beneficial organisms (or characteristics thereof) present on or near the plants 106. As yet another example, each human scout 110 may carry one or more instruments that can be used to perform instrument-based inspections of the plants 106. As still another example, each human scout 110 may use or have access to a cart 111 or other portable equipment that carries one or more instruments that can be used to perform instrument-based inspections of the plants 106. As a particular example, ECOATION INNOVATIVE SOLUTIONS INC. offers various products that can be used in greenhouses or other locations, such as the OKO manually-driven cart (which includes an interactive display that can be used by an operator and one or more cameras or other sensors).

In this example, each human scout 110 may carry or otherwise have access to a tablet computer or other mobile electronic device 112, which the human scout 110 may use to provide or retrieve data. For example, each human scout 110 may use a mobile electronic device 112 to capture still, video, or thermal images of plants 106 being inspected, identify any fruits/vegetables/flowers/other production associated with the plants 106 being inspected, identify any pests/diseases/other conditions associated with the plants 106 being inspected, or identify any beneficial organisms associated with the plants 106 being inspected. Note that the mobile electronic device 112 may be a handheld device or may be incorporated into a larger mobile device, such as an OKO cart or other cart 111. Also note that still, video, or thermal images of plants 106 may be captured in any suitable manner, such as standard two-dimensional (2D) imaging, 360° imaging, or stereoscopic three-dimensional (3D) imaging (which may be created with either 2D plus depth information or a combination of left and right video information).

Each mobile electronic device 112 may also identify its location in order to associate captured information or to provide useful information related to one or more plants 106 at or near its location. For example, a mobile electronic device 112 may identify its location and associate any information input by a human scout 110 or any information captured by one or more sensors with that location. This may allow, for instance, the mobile electronic device 112 to automatically associate information input by the human scout 110 or captured by one or more sensors with that location or with one or more plants 106 at or near that location. As another example, a mobile electronic device 112 may identify its location and output to a human scout 110 any pests or diseases previously identified at or near its location or any pests or diseases projected to now exist at or near its location. Note, however, that in other embodiments the identification of the location of a mobile electronic device 112 may occur in another component external to the mobile electronic device 112, in which case the external component may be responsible for associating captured information with the mobile electronic device's location or for providing information based on the mobile electronic device's location.

Any suitable technique may be used to identify a location of each mobile electronic device 112, such as manual input from a user, the use of Global Positioning System (GPS) or Ultra-Wideband (UWB) positioning, the scanning of optical tags (such as bar codes or QR codes), or the transmission or receipt of radio frequency identification (RFID) signals or other wireless signals. Note that this disclosure is not limited to any particular location identification technique. The specific location identification technique(s) used in the system 100 can vary as needed or desired, and a location identification technique may be used within or external to the mobile electronic devices 112. Also, a determined location may be expressed in any suitable manner, such as row/post numbers, GPS coordinates, or other expression of location.

One or more mobile sensory platforms 114 (also referred to as robotic scouts 114) may also or alternatively be employed to move around the one or more growing areas 104a-104n and to automatically inspect the plants 106. For example, each robotic scout 114 may include one or more cameras for capturing still, video, or thermal images of plants 106 being inspected, one or more sensors for measuring one or more aspects associated with the plants 106 being inspected, or other components configured to collect measurement data associated with the plants 106 being inspected. Again, still, video, or thermal images of plants 106 may be captured in any suitable manner, such as standard 2D imaging, 360° imaging, or stereoscopic 3D imaging. Each robotic scout 114 may include any suitable type(s) of sensor(s) or other measurement device(s), such as one or more physiological sensors, surface analysis sensors, chemical sensors, thermal sensors, microclimate sensors, image-based or video-based sensors, spectroscopy sensors, volatile organic compound sensors, or canopy scanning sensors. Note that the same type(s) of sensor(s) may also or alternatively be used by the human scouts 110 or by carts 111 or other electronic devices 112 used by the human scouts 110, or the human and robotic scouts 110 and 114 may use different types of sensors.

Each robotic scout 114 may also identify its location or engage in actions that allow an external component to identify its location. Any suitable technique may be used by each robotic scout 114 or another component to identify a location of the robotic scout 114, and determined locations may be expressed in any suitable manner. Example techniques may include the use of GPS or UWB positioning, the scanning of optical tags (such as bar codes or QR codes), or the transmission or receipt of RFID signals or other signals. Again, note that this disclosure is not limited to any particular location identification technique(s), and a location identification technique may be used within or external to each robotic scout 114.

Any suitable type(s) of robotic scout(s) 114 may be used in the system 100 to automatically inspect plants 106 in one or more growing areas 104a-104n. In some embodiments, example implementations of the robotic scouts 114 are provided in U.S. Pat. No. 10,241,097; U.S. Patent Application Publication No. 2017/0032258; and U.S. patent application Ser. No. 16/990,212 (all of which are hereby incorporated by reference in their entirety). In other embodiments, the IRIS SCOUTROBOT robotic scout from ECOATION INNOVATIVE SOLUTIONS INC. may be used. Note, however, that this disclosure is not limited to use with any particular type of robotic scout 114.

At least one network 116 may be used to facilitate communications between various components of the system 100. For example, the network 116 may communicate Internet Protocol (IP) packets, frame relay frames, Asynchronous Transfer Mode (ATM) cells, or other suitable information between network addresses. The network 116 may include one or more local area networks (LANs), metropolitan area networks (MANs), wide area networks (WANs), all or a portion of a global network such as the Internet, or any other communication system or systems at one or more locations. The network 116 may also operate according to any appropriate communication protocol or protocols. The network 116 may include one or more public networks and/or one or more private networks. In some cases, the network 116 may include at least one wireless network that facilitates wireless communications with the mobile electronic devices 112 and the robotic scouts 114, as well as at least one wired network that facilitates wired communications. Note that the network 116 may or may not represent a network associated exclusively with one or more individual growing areas 104a-104n. As a particular example, the network 116 may represent a 5G network that can provide mobile data communication services over a specified area that includes at least one growing area 104a-104n.

In some cases, one or more other data sources 118 may be provided for a growing area. The one or more other data sources 118 represent data sources separate from the human and robotic scouts 110, 114. These other data sources 118 may represent any other suitable source(s) of data related to the growing of the plants 106. For example, the other data sources 118 may include one or more fixed sensors located at one or more points in or around the one or more growing areas 104a-104n. These fixed sensors may be used to collect any suitable information, such as natural or artificial lighting conditions, humidity, or other conditions that affect multiple plants 106 or multiple growing areas 104a-104n. As a particular example, the other data sources 118 may include fixed "climate boxes" that include various sensors for measuring climatic conditions, where the climate boxes are positioned every few acres in a growing area. The other data sources 118 may also or alternatively include external sources of information, such as predicted near-term weather or predicted long-term climate conditions.

Note that while all growing areas 104a-104n are shown here as having a common layout, each growing area 104a-104n may include all or a subset of the illustrated components in any suitable arrangement. Also note that the growing areas 104a-104n may have common or different arrangements. Thus, for example, one or some of the growing areas 104a-104n may use only human scouts 110 with electronic devices 112, one or some of the growing areas 104a-104n may use only robotic scouts 114, and one or some of the growing areas 104a-104n may use a combination of human and robotic scouts 110, 114. As another example, each of the growing areas 104a-104n may or may not include or be associated with one or more other data sources 118. In general, each of the growing areas 104a-104n may include at least one source of plant-related data for the plants 106 in that growing area (whether human, robotic, or other).

The data processing platform 102 is communicatively coupled to the network 116 and is configured to process data collected or provided by the mobile electronic devices 112, the robotic scouts 114, and/or the other data sources 118. The data processing platform 102 can also interact with the mobile electronic devices 112 and the robotic scouts 114, such as by providing data to the mobile electronic devices 112 for use by the human scouts 110 and by providing data to the robotic scouts 114 to control scouting.

As described in more detail below, in some embodiments, the data processing platform 102 processes collected data in order to identify spatial production anomalies associated with the plants 106 in one or more growing areas 104a-104n. In other embodiments, the data processing platform 102 processes collected data in order to at least partially remove time of day variations from data associated with the plants 106 in one or more growing areas 104a-104n. In still other embodiments, the data processing platform 102 processes collected data in order to identify more favorable growing and environmental conditions associated with at least one plant genotype or phenotype based on the growth of the plants 106 in multiple growing areas 104a-104n. Example operations that may be performed by the data processing platform 102 to support these functions are described in more detail below. Note that the data processing platform 102 may support one, some, or all of these functions depending on its implementation.

Note that the data processing platform 102 may also be configured to generate and process "synthetic data," such as data that is calculated based on data collected or provided by the mobile electronic devices 112, the robotic scouts 114, and/or the other data sources 118. As a particular example, synthetic data may be obtained by applying one or more mathematical models of at least one greenhouse or other growing area 104a-104n to obtained sensor measurements or other data measurements. These models may represent any suitable type(s) of mathematical model(s), such as one or more first-principles biological-physical models of plant growth. Among other things, these models may permit users to perform simulation experiments to explore plant responses under a wide variety of conditions. The phrase "data measurements" as used in this document includes any suitable data values, whether those data values are captured by sensors, calculated using one or more equations, derived using one or more models, or obtained in other ways.

Figure 2:
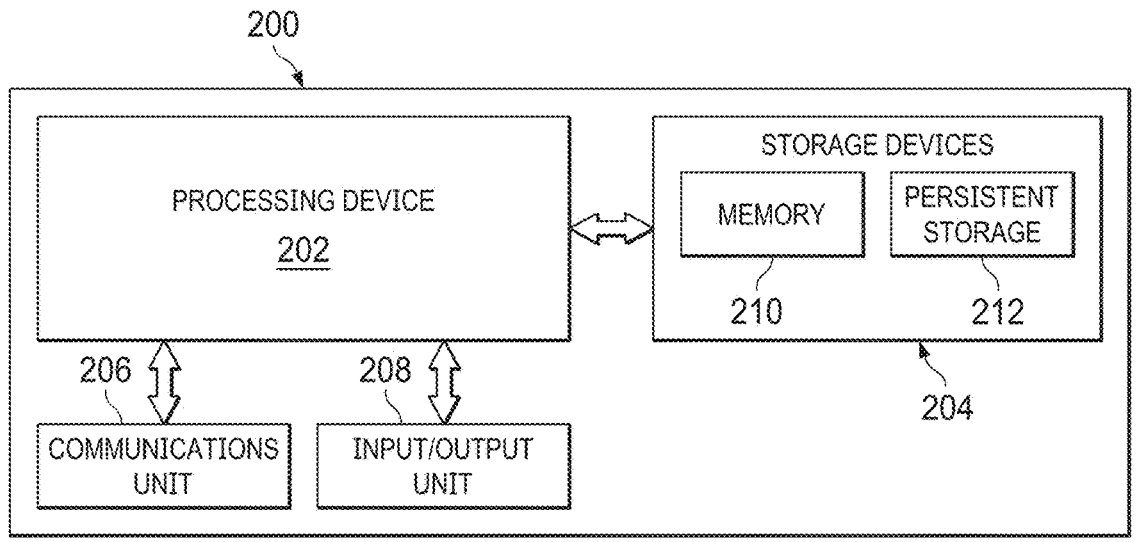
FIG. 2 illustrates an example device for collecting and processing plant-related data according to this disclosure.

The data processing platform 102 includes any suitable structure configured to process plant-related data and to perform one or more functions using the plant-related data. For example, the data processing platform 102 may represent at least one desktop computer, laptop computer, server computer, or other computing device. The data processing platform 102 may be local to or remote from the one or more growing areas 104a-104n. In some cases, for instance, the data processing platform 102 may be implemented in a cloud-based environment or using one or more remote servers. Among other things, this may allow a service provider to provide its data processing capabilities to a number of growers over a small or wide geographic area. This may also allow a service provider to collect a large amount of data related to a large number of plants 106 being grown, which the service provider may then process in order to perform various functions. However, the data processing platform 102 may be implemented in any other suitable manner. One example of the data processing platform 102 is shown in FIG. 2, which is described below.

In some cases, the data processing platform 102 may communicate with one or more additional users 120 in one or more of the growing areas 104a-104n. The one or more additional users 120 may use one or more electronic devices 122. The additional users 120 may represent any suitable users associated with the plants 106 or the growing areas 104a-104n, such as one or more experts, non-experts, growers, or crop-site managers. The electronic devices 122 may represent any suitable electronic devices for interacting with the data processing platform 102, such as desktop computers, laptop computers, tablet computers, or mobile smartphones. The users 120 and their electronic devices 122 may be located local to or remote from the one or more growing areas 104a-104n.

The data processing platform 102 can implement various functions that are described in more detail below. For example, in some embodiments, the data processing platform 102 may process plant-related data to perform real-time identification and resolution of spatial production anomalies in agriculture. In these embodiments, the data processing platform 102 can obtain plant production data, physical plant data, climate data, pest and disease data, crop work data, and crop treatment data (all of which are described above) or other data related to the plants 106 in one or more growing areas 104a-104n. The data processing platform 102 can perform one or more analyses of the collected data and generate one or more visualizations based on the analyses. Various types of analyses may be performed by the data processing platform 102. For instance, one or more analyzes may be performed to identify specific plants 106 in or zones of at least one growing area 104a-104n that are experiencing plant production issues (such as under-production or over-production) and to identify one or more potential causes of the plant production issues. The visualizations can be used to graphically identify the plant production issues and optionally to present one or more potential causes of the plant production issues and/or potential resolutions for the plant production issues.

In other embodiments, the data processing platform 102 may process collected plant-related data that might be subject to "time of day" variations. For example, temperature measurements or gas measurements (such as carbon dioxide, oxygen, or nitrogen dioxide measurements) can often vary depending on the time of day that the measurements are captured. This can cause problems in the interpretation of data. For example, a temperature measurement may be taken at a location in a greenhouse and determined to be high. However, it may be important to understand whether the temperature was high because the entire greenhouse was warm (such as during early to mid-afternoon) or because that area of the greenhouse is consistently warmer than average. The former case may be understood as "normal operation," while the latter case may represent a spatial anomaly that can impact plant performance and may require corrective action. It is therefore necessary or desirable to be able to parse data so that the appropriate action(s) may be taken (if at all).

In these embodiments, the data processing platform 102 can process the plant-related data to identify at least one baseline that shows how one or more types of measurements can vary by time of day for a specific growing area 104a-104n. The data processing platform 102 can then use the at least one baseline to normalize or otherwise process measurements in order to at least partially remove the effects of the time of day from the measurements. The data processing platform 102 may store, output, or use the adjusted measurements in any suitable manner, such as to perform real-time identification and resolution of spatial production anomalies or to identify improved or optimal growing and environmental conditions for plant genotypes and phenotypes. This allows more accurate operations to occur using the collected measurements. This process can be performed for each growing area 104a-104n, which is useful since growing areas 104a-104n are rarely completely uniform in their climatic conditions or other conditions.

In still other embodiments, the data processing platform 102 may process collected plant-related data for plants 106 with at least one genotype or phenotype being grown under various growing and environmental conditions, such as in different growing areas 104a-104n (or portions thereof). The data processing platform 102 may process the data in order to identify the conditions that result in desired plant characteristics being expressed while the plants 106 are being grown under the different growing and environmental conditions. This can be based on a large amount of data related to a large number of plants 106 growing under different conditions in the growing area(s) 104a-104n. The identified conditions may be used to make recommendations to growers on how to best grow plants from seeds, cuttings, or tissue culture materials, to provide production guarantees to growers, or to perform other functions. The improved or optimal growing and environmental conditions may be identified in significantly shorter times compared to prior approaches.

Additional details regarding these three functions are provided below. As noted above, the data processing platform 102 may support one, some, or all of these functions depending on the implementation. There is no requirement that the data processing platform 102 support all three of these functions in each implementation of the data processing platform 102.

Although FIG. 1 illustrates one example of a system 100 for collecting and processing plant-related data, various changes may be made to FIG. 1. For example, the system 100 may include any suitable number of plants 106 in any suitable number of growing areas 104a-104n, and the plants 106 may be inspected by any suitable number of human scouts 110 and/or robotic scouts 114. Also, the system 100 may include any suitable number of data processing platforms 102, and components such as networks 116 and other data sources 118 may or may not be shared across multiple growing areas 104a-104n. Further, each growing area 104a-104n may be associated with any suitable number of human scouts 110, electronic devices 112, robotic scouts 114, networks 116, and other data sources 118 (including none of one or more of these components). In addition, the system 100 may interact with any suitable number of additional users 120 in one or more of the growing areas 104a-104n.

FIG. 2 illustrates an example device 200 for collecting and processing plant-related data according to this disclosure. One or more instances of the device 200 may, for example, be used to at least partially implement the functionality of the data processing platform 102 of FIG. 1. However, the functionality of the data processing platform 102 may be implemented in any other suitable manner. Also, the same or similar arrangement of components as shown in FIG. 2 may be used to at least partially implement the functionality of one or more of the electronic devices 112, 122 in FIG. 1. However, the functionality of each electronic device 112, 122 may be implemented in any other suitable manner. In addition, the same or similar arrangement of components as shown in FIG. 2 may be used to at least partially implement the functionality of each robotic scout 114 in FIG. 1. However, the functionality of each robotic scout 114 may be implemented in any other suitable manner.

As shown in FIG. 2, the device 200 denotes a computing device or system that includes at least one processing device 202, at least one storage device 204, at least one communications unit 206, and at least one input/output (I/O) unit 208. The processing device 202 may execute instructions that can be loaded into a memory 210. The processing device 202 includes any suitable number(s) and type(s) of processors or other devices in any suitable arrangement. Example types of processing devices 202 include one or more microprocessors, microcontrollers, digital signal processors (DSPs), application specific integrated circuits (ASICs), field programmable gate arrays (FPGAs), or discrete circuitry.

The memory 210 and a persistent storage 212 are examples of storage devices 204, which represent any structure(s) capable of storing and facilitating retrieval of information (such as data, program code, and/or other suitable information on a temporary or permanent basis). The memory 210 may represent a random access memory or any other suitable volatile or non-volatile storage device(s). The persistent storage 212 may contain one or more components or devices supporting longer-term storage of data, such as a read only memory, hard drive, Flash memory, or optical disc.

The communications unit 206 supports communications with other systems or devices. For example, the communications unit 206 can include a network interface card or a wireless transceiver facilitating communications over a wired or wireless network, such as a network 116. The communications unit 206 may support communications through any suitable physical or wireless communication link(s).

The I/O unit 208 allows for input and output of data. For example, the I/O unit 208 may provide a connection for user input through a keyboard, mouse, keypad, touchscreen, or other suitable input device. The I/O unit 208 may also send output to a display, printer, or other suitable output device. Note, however, that the I/O unit 208 may be omitted if the device 200 does not require local I/O, such as when the device 200 can be accessed remotely.

In some embodiments, the instructions executed by the processing device 202 can include instructions that implement the functionality of the data processing platform 102. For example, the instructions executed by the processing device 202 may cause the processing device 202 to analyze data collected about various plants 106, such as data from one or more human scouts 110 (via one or more mobile electronic devices 112), one or more robotic scouts 114, and/or one or more other data sources 118, to perform real-time identification and resolution of spatial production anomalies associated with the plants 106. The instructions executed by the processing device 202 may also or alternatively cause the processing device 202 to analyze data collected about various plants 106 in order to at least partially remove the effects of time of day variations from certain measurements. The instructions executed by the processing device 202 may also or alternatively cause the processing device 202 to analyze data collected about various plants 106 in order to identify improved or optimal growing and environmental conditions for specific plant genotypes and phenotypes. The instructions executed by the processing device 202 can further cause the processing device 202 to output its results, such as by providing visualizations or other outputs to one or more human scouts 110 (via one or more mobile electronic devices 112), one or more robotic scouts 114, and/or one or more additional users 120 (via one or more electronic devices 122).

Although FIG. 2 illustrates one example of a device 200 for collecting and processing plant-related data, various changes may be made to FIG. 2. For example, computing devices/systems, mobile electronic devices, and robotic scouts can come in a wide variety of configurations, and FIG. 2 does not limit this disclosure to any particular computing device or system, to any particular mobile electronic device, or to any particular robotic scout.

Figure 3:
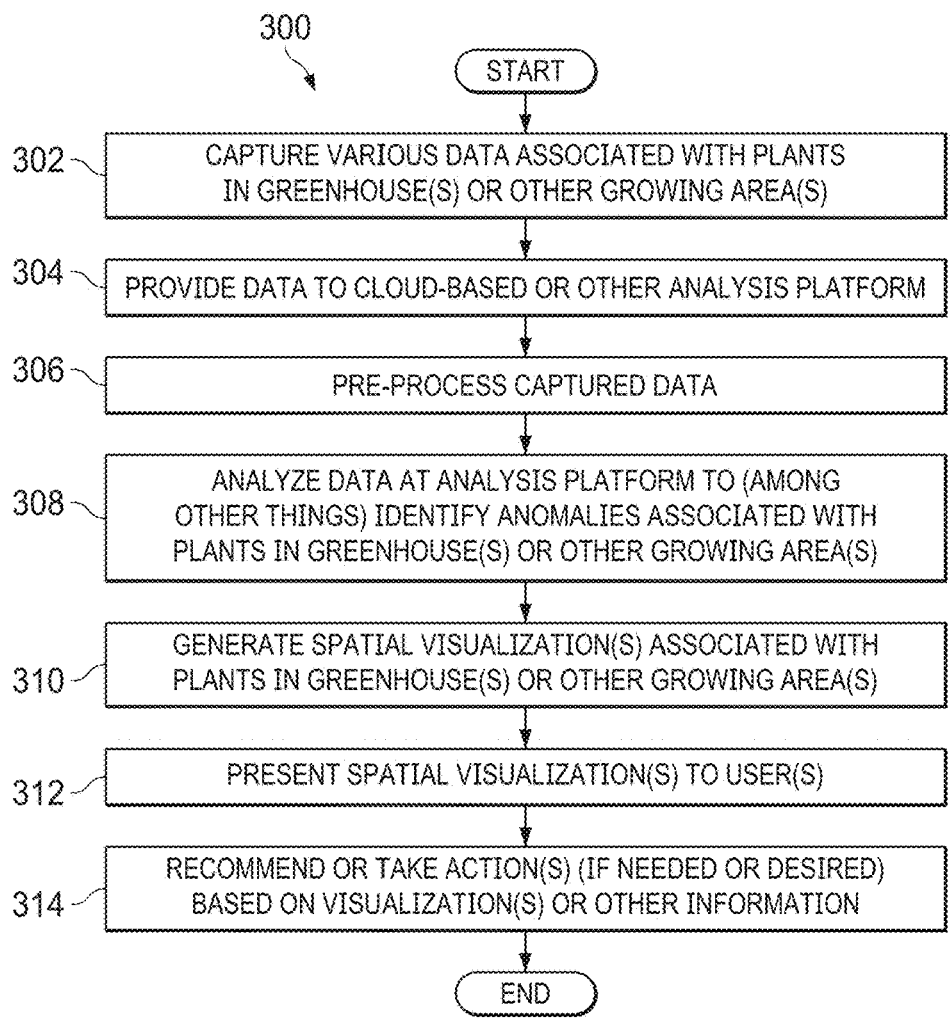
FIG. 3 illustrates an example method for real-time identification and resolution of spatial production anomalies in agriculture according to this disclosure.

FIG. 3 illustrates an example method 300 for real-time identification and resolution of spatial production anomalies in agriculture according to this disclosure. For ease of explanation, the method 300 is described as being performed using the system 100 of FIG. 1, including the data processing platform 102 (which may be implemented using the device 200 of FIG. 2). However, the method 300 may be performed using any suitable device(s) in any suitable system(s).

As shown in FIG. 3, various data associated with plants in one or more greenhouses or other growing areas is captured at step 302. This may include, for example, one or more human scouts 110 and/or one or more robotic scouts 114 recording or capturing various data associated with the plants 106 in one or more growing areas 104a-104n or with the one or more growing areas 104a-104n. This may also include one or more other data sources 118 recording or capturing various data related to the plants 106 in one or more growing areas 104a-104n or related to the one or more growing areas 104a-104n. The captured data may include plant production data, physical plant data, climate data, pest and disease data, crop work data, and crop treatment data. Any subset or all of the various plant production data, physical plant data, climate data, pest and disease data, crop work data, and/or crop treatment data described above may be captured and used here. At least some of the data measurements here may be associated with locations at which the data measurements were captured, such as row/post numbers, GPS coordinates, or other location information.

The captured data is provided to a cloud-based or other analysis platform at step 304. This may include, for example, the data processing platform 102 obtaining the captured data for each growing area 104a-104n via one or more networks 116. The captured data may be provided to the data processing platform 102 in any suitable manner. Depending on the implementation, data may be provided to the data processing platform 102 in real-time, on demand, opportunistically whenever wireless or other communication channels are available, or in some other way. Note that various data measurements may also be derived by the data processing platform 102 based on data received from the human scouts 110, robotic scouts 114, other data sources 118, or other sources. This may occur, for instance, when the data processing platform 102 applies at least one algorithm to images or other data obtained by the data processing platform 102.

The captured data may be pre-processed at step 306. This may include, for example, the data processing platform 102 filtering the captured data and removing bad or invalid data. This may also include the data processing platform 102 performing the technique described below to at least partially remove time of day variations from at least some of the captured data.

The captured and optionally pre-processed data is analyzed at step 308. This may include, for example, the data processing platform 102 processing the captured and pre-processed data in order to identify spatial distributions of plant production, pests, diseases, climatic conditions, or other characteristics within the one or more growing areas 104a-104n, patterns in the data, and correlations between different data. Part of this processing may involve the data processing platform 102 identifying any anomalies associated with production by the plants 106 in the one or more greenhouses or other growing areas 104a-104n, such as by identifying under-producing or over-producing plants 106 or zones of the growing areas 104a-104n. Examples of the types of processing that may occur here are provided below. Note, however, that anomalies may be identified later in the process, such as after information has been displayed to a user. Also note that the data processing platform 102 itself may not identify anomalies and that one or more users may identify anomalies (and possibly provide an identification of those anomalies to the data processing platform 102).

The analysis results may be used in various ways. For instance, one or more spatial visualizations associated with the plants in the one or more greenhouses or other growing areas may be generated at step 310 and presented to one or more users at step 312. This may include, for example, the data processing platform 102 generating spatial representations of climate data along with plant production data or pest/disease data, which may be useful in identifying how plant production, pests, or diseases vary by climate. This may also include the data processing platform 102 generating a time progression of spatial plant production data along with spatial climate data or spatial pest/disease data, which may be useful in identifying how plant production varies over time based on climate, pests, or diseases. Several examples of the types of visualizations that may be generated and presented are described below. However, it should be noted that visualizations can vary widely based on, among other things, the data available for use and the requirements of particular users.

As another example, one or more actions may be recommended or taken (if needed or desired) based on at least one of the visualizations or other information at step 314. In some cases, this may include an expert grower determining whether one or more particular treatments should be deployed or whether one or more control systems (such as for one or more pieces of the equipment 108) should be adjusted. In other cases, this may include a consultant recommending whether new treatments should be used or whether growing and environmental conditions should be changed. In still other cases, this may include the data processing platform 102 generating a list of possible changes to one or more growing or environmental conditions that might result in improved production by one or more plants 106. Other examples of actions that might be taken are provided below and can vary based on the specific circumstances (including the specific plants 106 and the specific anomalies). Depending on the timing, an action may be implemented during the current growing season (in order to affect the plants 106 currently being grown) or during a subsequent growing season (in order to affect the plants 106 to be grown in the future).

The method 300 shown in FIG. 3 may occur once or more than once for each growing area 104a-104n or collection of growing areas 104a-104n. For example, in some embodiments, the method 300 shown in FIG. 3 may be performed continuously, periodically, or intermittently during growth of various plants 106 in each of one or more growing areas 104a-104n. When implemented in this manner, the effect(s) of any corrective action(s) from step 314 can be identified through continued or additional monitoring of the plants 106 subject to the corrective action(s), and the corrective action(s) may continue to be applied (or one or more different corrective actions may be identified and applied) until a desired result is obtained. For instance, the reaction of one or more plants 106 to the corrective action(s) may be identified using additional data, and a determination can be made whether to continue the corrective action(s), cease the corrective action(s), or perform other or additional corrective action(s). This may help to provide one or more corrective actions in order to resolve at least one noted plant production issue with one or more plants 106. As a particular example, this may allow one or more characteristics of the plants 106 to be monitored in order to determine whether one or more corrective actions might be needed or desired to help at least one genotype or phenotype trait of the plants 106 to be expressed. This can effectively help keep the plants 106 more or fully on their genotypical and phenotypical "track," thereby helping to improve or guarantee production from the particular genotype. In other embodiments, the method 300 shown in FIG. 3 may be performed once in order to alter how plants 106 are being grown during a current growing season or to alter how plants 106 might be grown during a subsequent growing season. In general, the frequency of the method 300 can easily vary as needed or desired.

In some embodiments, one or more machine learning algorithms may be applied in order to generate or derive at least some of the data used by the data processing platform 102. For example, still, video, or thermal images of various plants 106 may be captured, such as by one or more human scouts 110 using one or more cameras or other electronic devices 112, by one or more carts 111 used by the one or more human scouts 110, or by one or more robotic scouts 114. One or more machine learning algorithms in the electronic devices 112, carts 111, or robotic scouts 114 may be applied to the captured images, or the captured images may be provided to the data processing platform 102 or other device or system that supports one or more machine learning algorithms. However implemented, the one or more machine learning algorithms may be applied to the captured images in order to identify or derive at least some of the plant production data, physical plant data, pest and disease data, crop work data, or crop treatment data.

As a particular example, a neural network or other machine learning algorithm may be applied to still, video, or thermal images captured of various plants 106, where the neural network or other machine learning algorithm is trained to detect and count specific instances of fruits, vegetables, ornamental flowers, or other production items produced by the plants 106. The neural network or other machine learning algorithm may also be trained to identify, based on color or other factors, the ripeness or ready states of the fruits, vegetables, ornamental flowers, or other production items produced by the plants 106. This allows image processing to be used to automatically estimate production by the plants 106.

As another particular example, a neural network or other machine learning algorithm may be applied to still, video, or thermal images captured of various plants 106, where the neural network or other machine learning algorithm is trained to count the number of plant stems in a given area (in order to identify the stem density in that area). Stem density is an indicator of the quality of the crop work being performed. Certain types of plants 106, such as cucumber and tomato plants, may be adjusted regularly in a process known as "lowering." Anomalies in crop density (such as packing plants 106 too densely) are known to impact plant production, and these conditions may be detected by or using the neural network or other machine learning algorithm. This allows image processing to be used to automatically identify characteristics related to crop work or other characteristics that might impact plant production.

Various models may also be developed and used by the data processing platform 102 to support various functions. For example, pest and disease data may be collected by the human scouts 110 or the robotic scouts 114 and used to produce one or more spatiotemporal models. The one or more spatiotemporal models may represent how at least one pest or disease can spread in at least one growing area 104a-104n and how the pest(s) or disease(s) might respond to one or more treatments. One or more spatiotemporal models may similarly be produced to identify how at least one biocontrol agent (such as a beneficial organism) can spread in at least one growing area 104a-104n over time. Each spatiotemporal model may be generated in any suitable manner, such as by analyzing data associated with at least one pest, disease, or biocontrol agent over time (which may or may not be in the same growing area to which the spatiotemporal model is later applied). Projections about the spread of a particular pest, disease, or biocontrol agent over time in a growing area may then be calculated and used by the data processing platform 102 using the appropriate spatiotemporal model. Specific example techniques for generating spatiotemporal models and making projections using spatiotemporal models are provided in U.S. patent application Ser. No. 16/883,354 (which is hereby incorporated by reference in its entirety). However, various techniques for model identification are known, and additional techniques are sure to be developed in the future. This disclosure is not limited to any particular technique for identifying spatiotemporal models.

Other models may be generated by the data processing platform 102 or other component(s) and used to identify correlations or associations between different data collected in the system 100. For example, the analysis of captured data by the data processing platform 102 may indicate that a specific zone of a growing area 104a-104n is under-producing relative to other zones in the same growing area 104a-104n. The data processing platform 102 may analyze the data for that growing area 104a-104n (and possibly other growing areas) in order to generate one or more models that identify how one or more characteristics of the growing area 104a-104n might relate to plant production. As a particular example, the data processing platform 102 may analyze the data for a growing area 104a-104n and generate various models that identify how different pests/diseases and different climatic conditions of the growing area 104a-104n might relate to plant production. The data processing platform 102 may use the generated model(s) to make recommendations to one or more users on how conditions in the under-producing zone might be altered to increase plant production in the under-producing zone, or the data processing platform 102 may implement one or more changes itself to increase plant production in the under-producing zone. Ideally, this type of approach may be used to identify and resolve what may be the leading contributors to uneven production in at least one greenhouse or other growing area 104a-104n.

In general, models produced or used by the data processing platform 102 may have any suitable form. For example, as noted above, spatiotemporal models may be used to project how pests, diseases, or biocontrol agents can spread in one or more growing areas 104a-104n. As another example, patterns or associations between captured data for one or more growing areas 104a-104n (or portions thereof) may be visible simply through the generation and presentation of visualizations, such as when there is a clear association in the data between plant production and a specific pest. In those cases, the data processing platform 102 may simply identify a direct connection between specific characteristics, or a user may notice the association and provide information identifying a direct connection between specific characteristics to the data processing platform 102. More quantitative modeling may take the form of explanatory anomaly models (such as those produced using principal component analysis or partial least squares regression) or predictive dynamic models. Dynamic models may include model types such as auto-regressive moving average (ARMA) models or auto-regressive moving average with exogenous variable (ARMAX) models. Again, this disclosure is not limited to any particular type(s) of model(s) or any particular technique(s) for identifying models.

A simple linear version of an ARMAX model might be expressed as:

$$Y(t)=a \times Y(t-1)+b \times u_1(t)+c \times u_2(t)+d \times u_3(t)+ \quad (1)$$

Here, $Y(t)$ represents the current harvest count for plant production or other plant-related characteristic, and $Y(t-1)$ represents the previous harvest count for plant production or other plant-related characteristic. Also, $u_1$, $u_2$, and $u_3$ represent various characteristics that affect the plant production or other plant-related characteristic. In addition, a, b, c, and d represent model parameters of the ARMAX model, which can be identified during model training (a standard function). Note that the number of u terms and the number of model parameters can vary depending on the number of parameters that affect the plant-related characteristic. A more general nonlinear version of an ARMAX model might be expressed as:

$$Y(t)=f(u_1(t),u_2(t),u_3(t),\ldots,\theta) \quad (2)$$

where $\theta$ represents the model parameters. The model parameters may be obtained in various ways, such as by using first principles analysis or fitting to measured data. Note that models may be generated for any suitable plant-related characteristics in any suitable manner here.

One or more quantitative models may be used by the data processing platform 102 to make recommendations or implement changes to conditions associated with various plants 106, such as to try and make production from under-producing plants 106 closer to the production of other plants 106. For example, a model as defined in Equation (1) above may represent how a count of fruits or vegetables produced by plants 106 varies based on temperature, whitefly or other pest pressure, stem density, humidity, and carbon dioxide level. A derivative of the model relative to characteristic $u_1$ may be used to indicate that a steady-state change dY in fruit/vegetable size count Y requires a change in $u_1$ of:

$$dU_1=(1-a)/b \times dY \quad (3)$$

This allows specific recommendations to be determined and output to growers or other personnel. For instance, the data processing platform 102 may generate a graphical display or other output indicating that, for a particular under-performing zone of a growing area 104a-104n, a production increase might be obtained if one or more specific changes in growing and environmental conditions are made. As a particular example, the data processing platform 102 may generate a graphical display or other output indicating that a 1% increase in production count in a certain zone might be obtained by (i) increasing temperature in that zone by a first specified amount, (ii) decreasing whitefly pressure or other pest/disease pressure in that zone by a second specified amount, (iii) decreasing variability in stem density in that zone by a third specified amount, or (iv) decreasing humidity in that zone by a fourth specified amount while increasing carbon dioxide level in that zone by a fifth specified amount.

The exact recommendation(s) in any given situation can vary based on the one or more models produced or used by the data processing platform 102 and the specific plant-related measurements. In some cases, potential actions for indoor or protected crops might include personnel training in response to determining that a large number of plant heads are becoming broken (low stem count) or the density of stem placement is nonuniform. The potential actions for indoor or protected crops might also include, for pest- or disease-related issues, the identification of timings and dosages for pest- or disease-specific treatments or operational changes within a growing area 104a-104n to limit spread. The potential actions for indoor or protected crops might further include, for climate-related issues, the changing of one or more setpoints used by one or more computer-controlled climate systems, the repair or replacement of any faulty equipment, or the adding of additional equipment (such as one or more fans to improve airflow). The potential actions for indoor or protected crops might also include, for nutrient-related issues, the identification of types and dosages of nutrients or how the nutrients are delivered (such as application of fertilizer versus a "fertigation" system, which is an irrigation system that also delivers nutrients). In addition, the potential actions for indoor or protected crops might include, for water-related issues, adjustment to the amount of water delivered (such as via an irrigation or fertigation system). Any or all of these actions may be spatially varying, meaning different levels of actions or different types of actions may occur in different locations within a growing area. This kind of spatial dependence in actions performed supports what is often referred to as "precision agriculture." Also, any or all of these actions may be selected depending on the (spatial and temporal) measurements and models derived as discussed above.

In some cases, potential actions for outdoor or unprotected crops might include personnel training based on the identified quality of the crops. The potential actions for outdoor or unprotected crops might also include, for pest- or disease-related issues, the identification of timings and dosages for pest- or disease-specific treatments or operational changes within a growing area 104a-104n to limit spread. The potential actions for outdoor or unprotected crops might further include, for climate-related issues, the tracking of spatial microclimates in the outdoor environment (which may cause, for example, adjustments to other characteristics such as watering) and the tracking of macroclimates (which may require, for instance, adjustments to harvest timings). The potential actions for outdoor or unprotected crops might also include, for nutrient-related issues, the identification of types, dosages, and timings of fertilizer applications. In addition, the potential actions for outdoor or unprotected crops might include, for water-related issues, adjustment to the amount and timing of water delivered (such as via an irrigation system). Again, any or all of these actions may be spatially varying, meaning different levels of actions or different types of actions may occur in different locations within a growing area. Again, this kind of spatial dependence in actions performed supports precision agriculture. Also, any or all of these actions may be selected depending on the (spatial and temporal) measurements and models derived as discussed above.

One or more machine learning algorithms may also be applied in order to help identify any anomalies associated with the plants 106 being monitored. For example, a neural network or other machine learning algorithm may be trained to process various plant-related data and identify underproducing or over-producing plants or zones. As another example, a neural network or other machine learning algorithm may be trained to process various plant-related data and identify relationships between climate and pest or disease pressure or between plant production and climate or pest or disease pressure, where the relationships may be used to explain production anomalies.

Although FIG. 3 illustrates one example of a method 300 for real-time identification and resolution of spatial production anomalies in agriculture, various changes may be made to FIG. 3. For example, while shown as a series of steps, various steps in FIG. 3 may overlap, occur in parallel, occur in a different order, or occur any number of times.

Figure 4:
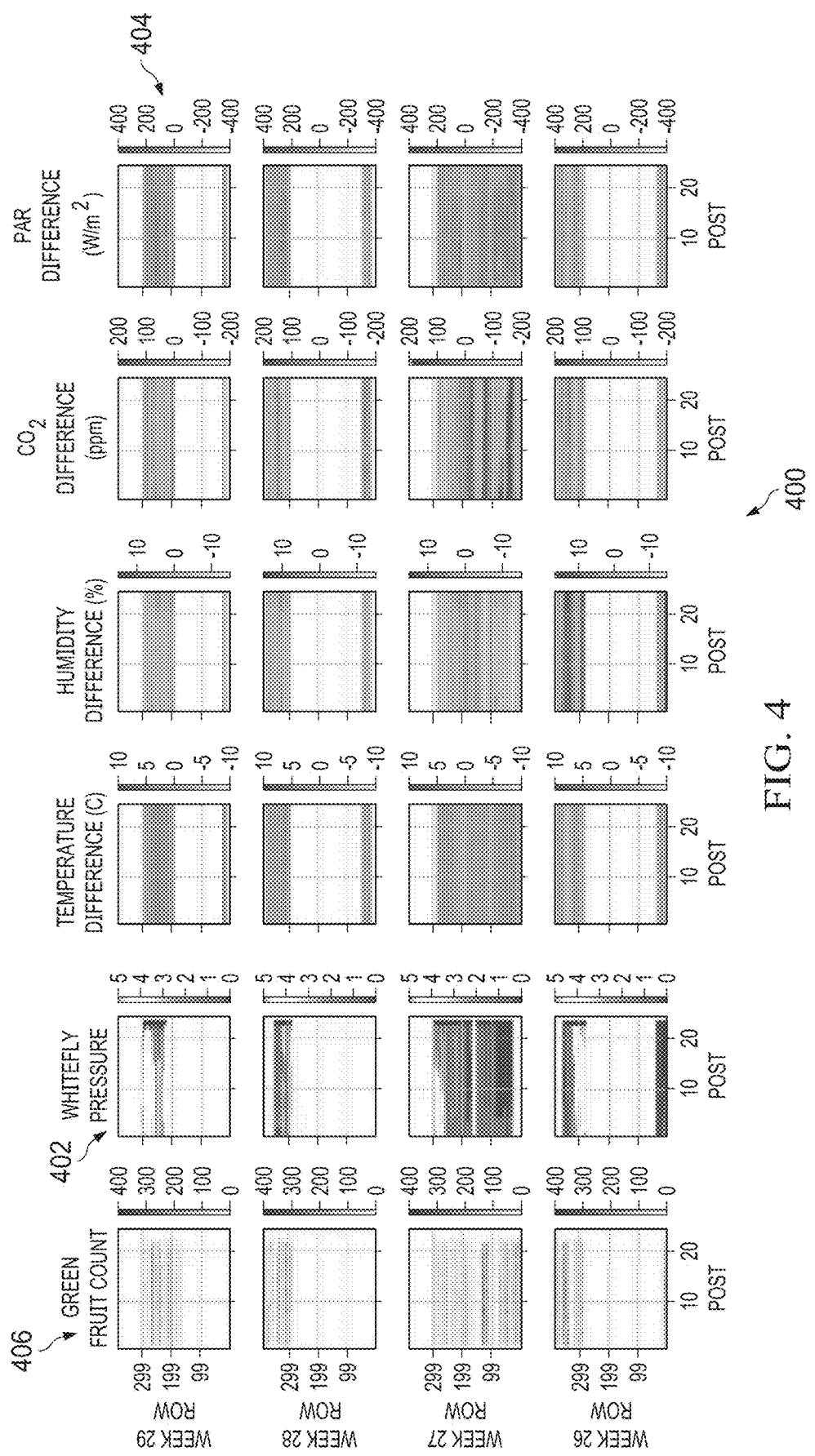
FIG. 4 illustrates an example visualization used for real-time identification of spatial production anomalies in agriculture according to this disclosure.

FIG. 4 illustrates an example visualization 400 used for real-time identification of spatial production anomalies in agriculture according to this disclosure. For ease of explanation, the visualization 400 may be described as being generated by the data processing platform 102 in the system 100 of FIG. 1 (which may be implemented using the device 200 of FIG. 2) during performance of the method 300 of FIG. 3. However, the visualization 400 may be generated using any suitable device(s) in any suitable system(s) during the performance of any suitable process(es). Also, it should be noted that the visualization 400 shown in FIG. 4 represents one example of a specific type of visualization that might be produced using the approaches described above, although any other suitable visualization may be generated by the data processing platform 102 as needed or desired.

As shown in FIG. 4, the visualization 400 includes a collection of various spatial maps 402. All of the spatial maps 402 here are associated with a common growing area 104a-104n, such as a greenhouse. The spatial maps 402 illustrate values of various plant-related characteristics by position in the common growing area 104a-104n. Here, the positions are based on row numbers and post numbers, although positions may be expressed in other ways. The spatial maps 402 thereby illustrate how the plant-related characteristics vary spatially within the common growing area 104a-104n.

Each spatial map 402 may plot values for a specific plant-related characteristic in any suitable manner, such as in absolute or relative terms. An absolute data value refers to a data value that is determined independent of other data values, while a relative data value refers to a data value that is determined based on at least one other data value. In FIG. 4, production count (such as fruit count) values and pest pressure values are expressed in absolute terms. That is, each production count value is within a scale from zero to four hundred and does not depend on other production count values, and each pest pressure value is within a scale from zero to five and does not depend on other pest pressure values. In contrast, temperature, humidity, carbon dioxide, and photosynthetically-active radiation (PAR) values or other illumination values are expressed in relative terms. Each of these values is expressed within positive and negative limits relative to at least one other value. Of course, the characteristics expressed in absolute and relative terms here are for illustration only, and each characteristic may be expressed in any suitable manner as needed or desired.

The spatial maps 402 in the visualization 400 are arranged in rows 404 and columns 406. In this example, each row 404 is associated with a different time period and includes spatial maps 402 associated with different characteristics. Also, in this example, each column 406 includes spatial maps 402 associated with the same characteristic. As a result, the visualization 400 illustrates a time progression of the different characteristics over a specified period of time. In this specific example, each time period is a week and the visualization 400 covers four weeks of overall time, although over time periods and overall times may be used. Also, a time progression may not be needed or desired, in which case a single row of spatial maps 402 might be presented.

Note that the visualization 400 can support any desired spatial fidelity and any desired temporal fidelity for the displayed data. Spatial fidelity generally refers to the level of spatial detail shown in the visualization 400, and temporal fidelity generally refers to the level of temporal detail shown in the visualization 400. In this example, the spatial fidelity used is at the row-post level, meaning different data values are provided for different row number-post number combinations within a growing area 104a-104n. Also, in this example, the temporal fidelity used is weekly, which may align with the decision-making schedule of many greenhouse operations. However, any other suitable spatial resolutions and temporal resolutions may be used here, and the spatial resolutions and temporal resolutions can vary in any suitable manner (such as based on user preference or the data being displayed).

The specific spatial maps 402 included in any given visualization 400 may be selected in any suitable manner. For example, at least one visualization 400 may be based on (i) a specific plant-related characteristic and (ii) any variables determined to have a significant relationship with or effect on that specific plant-related characteristic. Thus, in the example of FIG. 4, the data processing platform 102 (using the model identification techniques discussed above) may have determined that white fly or other pest pressure, temperature, humidity, carbon dioxide level, and photosynthetically-active radiation level or other illumination level all have significant impacts on plant production (at least relative to other variables). The identification of one or more key variables affecting a plant-related characteristic can be done in any suitable manner, and various techniques (such as those used to identify key performance indicators) may be used here. A user may also create or build the visualization 400 by selecting variables that the user knows or believes impact a specific plant-related characteristic. Different visualizations may be created for different plant-related characteristics, and the specific variables for those plant-related characteristics may be the same or different.

FIGS. 5A through 5D illustrate another example visualization 500 used for real-time identification of spatial production anomalies in agriculture according to this disclosure. For ease of explanation, the visualization 500 may be described as being generated by the data processing platform 102 in the system 100 of FIG. 1 (which may be implemented using the device 200 of FIG. 2) during performance of the method 300 of FIG. 3. However, the visualization 500 may be generated using any suitable device(s) in any suitable system(s) during the performance of any suitable process(es). Also, it should be noted that the visualization 500 shown in FIGS. 5A through 5D represents another example of a specific type of visualization that might be produced using the approaches described above, although any other suitable visualization may be generated by the data processing platform 102 as needed or desired.

Figure 5A:
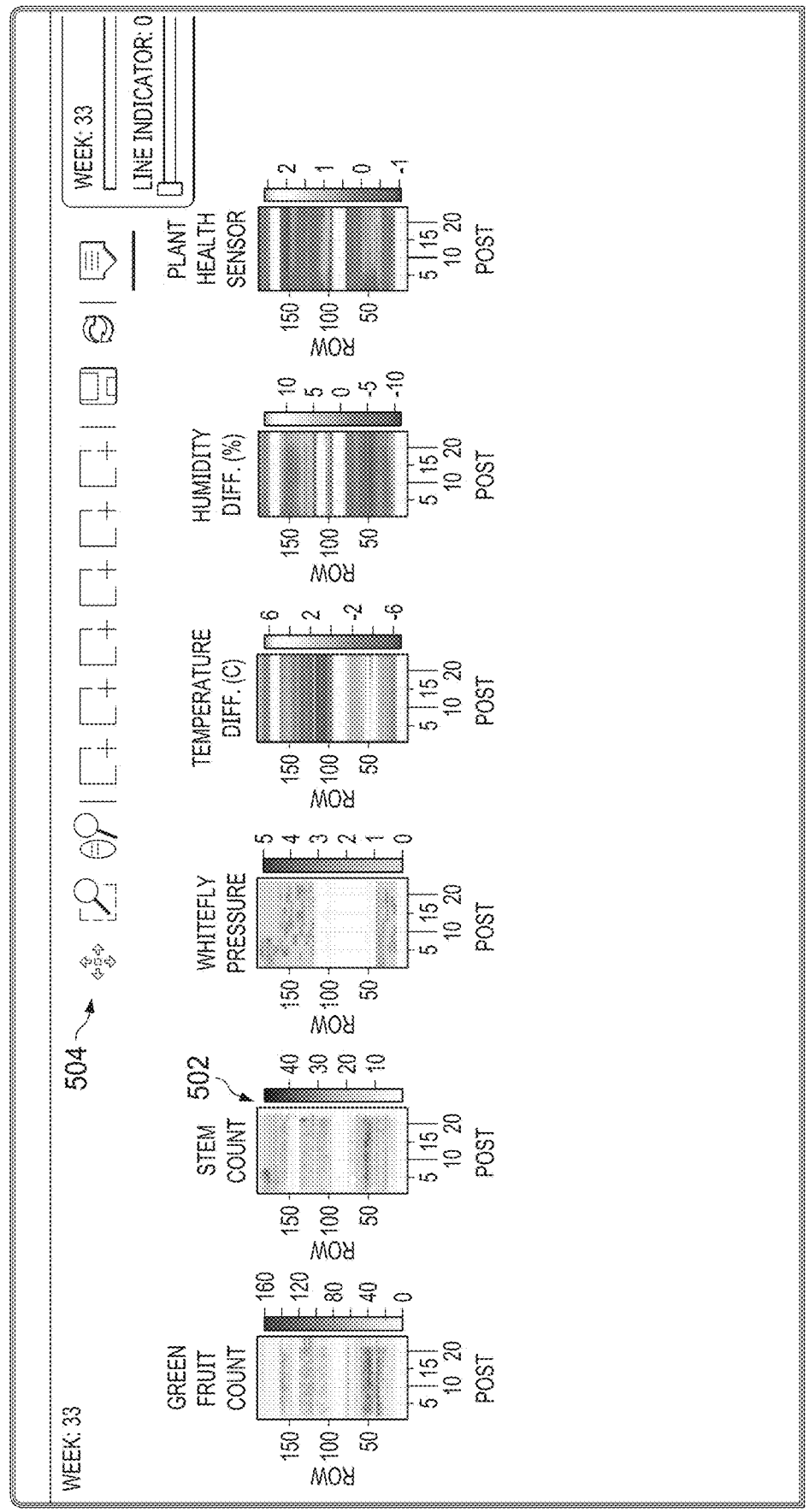
FIGS. 5A through 5D illustrate another example visualization used for real-time identification of spatial production anomalies in agriculture according to this disclosure.

As shown in FIG. 5A, the visualization 500 includes a collection of various spatial maps 502. All of the spatial maps 502 here are associated with a common growing area 104a-104n, such as a greenhouse. The spatial maps 502 illustrate values of various plant-related characteristics by position in the common growing area 104a-104n. Here, the positions are based on row numbers and post numbers, although positions may be expressed in other ways. The spatial maps 502 thereby illustrate how the plant-related characteristics vary spatially within the common growing area 104a-104n. Note that while multiple spatial maps 502 are shown here, a single spatial map 502 might be presented.

Each spatial map 502 may plot values for a specific plant-related characteristic in any suitable manner, such as in absolute or relative terms. In FIG. 5A, production count (such as green fruit count) values, stem count values, and pest pressure values are expressed in absolute terms. In contrast, temperature, humidity, and plant health values are expressed in relative terms. Of course, the characteristics expressed in absolute and relative terms here are for illustration only, and each characteristic may be expressed in any suitable manner as needed or desired. The spatial maps 502 in the visualization 500 are arranged in a single row, and the row is associated with a specific period of time (such as a particular week or other length of time). Note that the visualization 500 can support any desired spatial fidelity and any desired temporal fidelity for the displayed data. Any other suitable spatial resolutions and temporal resolutions may be used here, and the spatial resolutions and temporal resolutions can vary in any suitable manner (such as based on user preference or the data being displayed).

The specific spatial maps 502 included in any given visualization 500 may be selected in any suitable manner. For example, at least one visualization 500 may be based on (i) a specific plant-related characteristic and (ii) any variables determined to have a significant relationship with or effect on that specific plant-related characteristic. Thus, in the example of FIG. 5A, the data processing platform 102 (using the model identification techniques discussed above) may have determined that stem count, white fly or other pest pressure, temperature, humidity, and overall plant health all have significant impacts on plant production (at least relative to other variables). Again, the identification of one or more key variables affecting a plant-related characteristic can be done in any suitable manner, and various techniques (such as those used to identify key performance indicators) may be used here. A user may also create or build the visualization 500 by selecting variables that the user knows or believes impact a specific plant-related characteristic. Different visualizations may be created for different plant-related characteristics, and the specific variables for those plant-related characteristics may be the same or different.

Various controls 504 are provided in the visualization 500 that allow a user to invoke various functions associated with the visualization 500. For example, some of the controls 504 may allow a user to pan and zoom within each of the spatial maps 502, to save the current state of the visualization 500, to refresh the visualization 500, and to provide comments related to the visualization 500. Other controls 504 may allow a user to select a particular time period (such as a particular week) to view and to select a line indicator (which is described below) for specific data to be displayed.

Figure 5B:
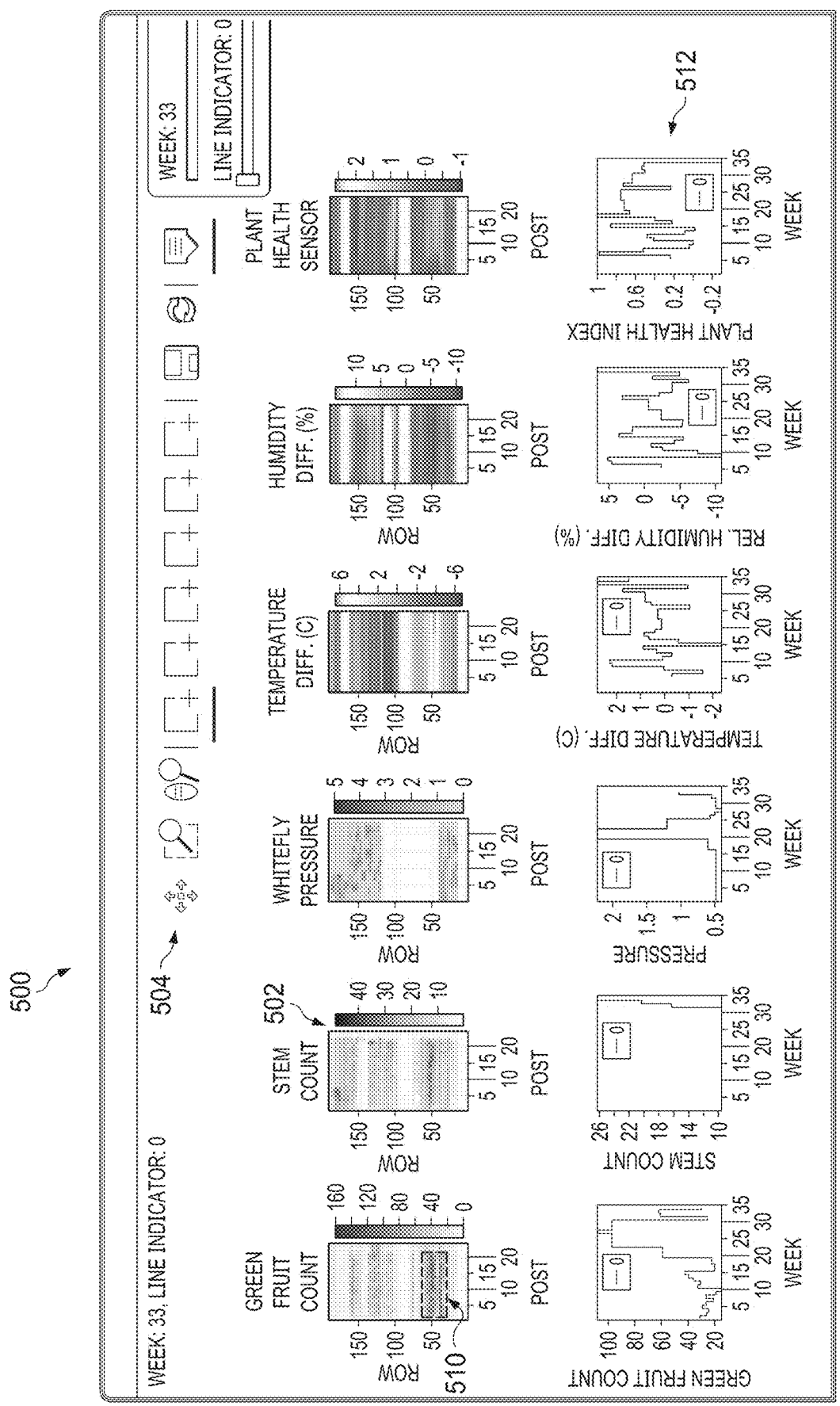

Still other controls 504 (represented as rectangles with plus signs) allow a user to select one or more portions of respective spatial maps 502 in order to view additional data related to the selected portion(s) of the spatial map(s) 502. As shown in FIG. 5B, a user may select one of these controls 504 and identify a selected area 510 in one of the spatial maps 502. The selected area 510 of the spatial map 502 corresponds to a selected portion of the growing area 104a-104n.

The selection of this area 510 can present the user with a number of additional visualizations, which in this example take the form of various graphs 512. Each graph 512 here corresponds to the variable associated with one of the spatial maps 502. Each graph 512 includes data for that variable plotted over time, but only for the selected portion of the growing area 104a-104n. The graphs 512 may be used by the user to, for example, identify why the number of green (unripened) production items is high in the selected portion of the growing area 104a-104n relative to other portions of the growing area 104a-104n. Note that the length of time over which data is plotted in the graphs 512 can be set or vary as needed or desired. Also note that the data shown in each graph 512 may represent any suitable data, such as actual data measurements or statistics associated with the actual data measurements (like mean/average data measurements, median data measurements, or trends).

Figure 5C:
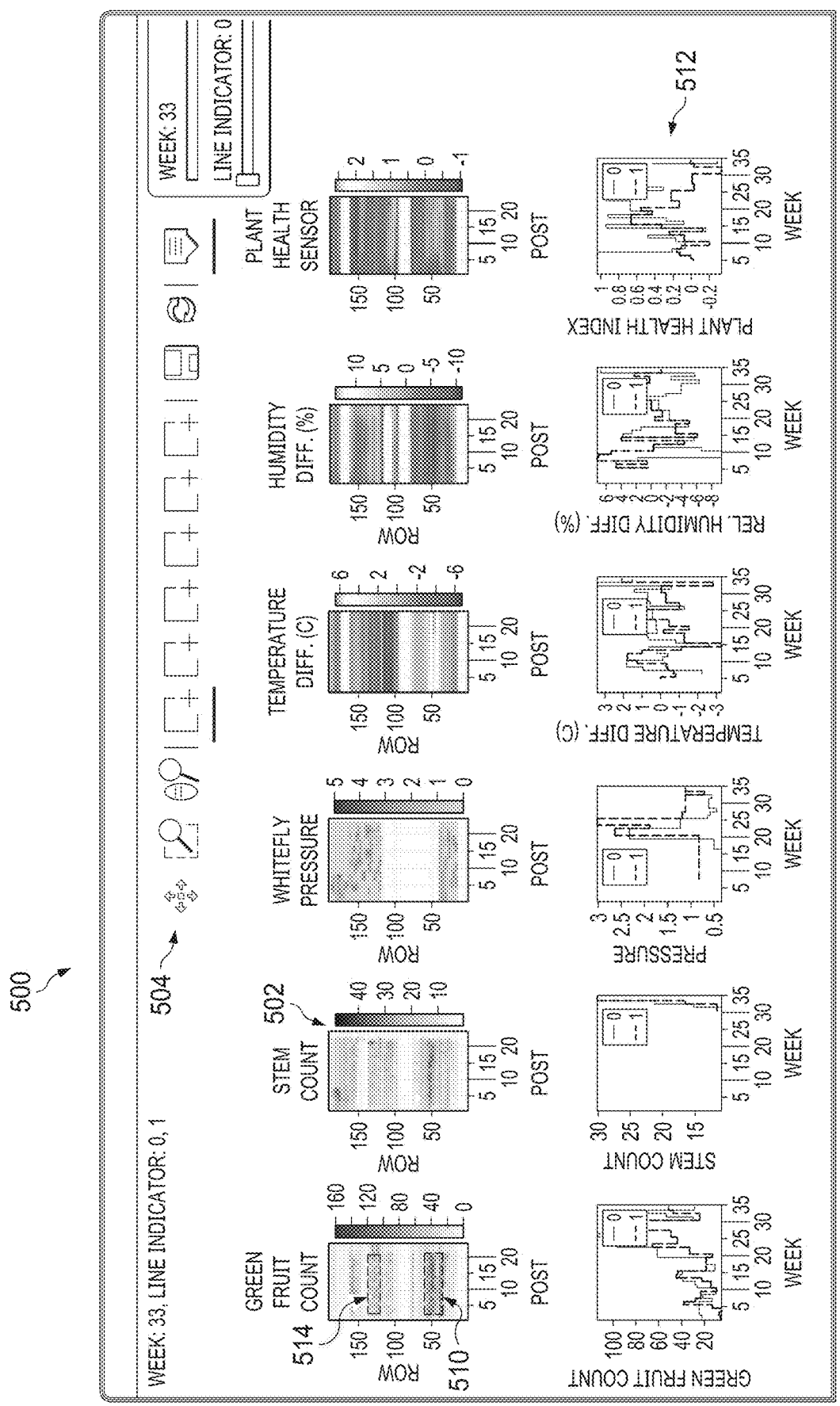

As shown in FIG. 5C, a user may select one or more of the controls 504 and identify multiple selected areas 510 and 514 in one or more of the spatial maps 502. Again, each selected area 510 and 514 of the spatial map 502 corresponds to a selected portion of the growing area 104a-104n. The graphs 512 are now updated with different lines associated with the different selected areas 510 and 514 of the spatial map 502. Note that while two areas have been selected here, a user may select more than two areas in one or more of the spatial maps 502.

This approach allows a user to select different portions of the growing area 104a-104n and to compare the values of the various variables associated with those portions of the growing area 104a-104n over time. The line indicator control here can be used to associate different lines in the graphs 512 with different selected areas 510, 514 in the spatial map(s) 502. For instance, the line indicator control can be used to cause data for different selected areas 510, 514 to be presented in the graphs 512 using different colors, line patterns, or other visual indicators. Note, however, that the different visual indicators for different lines or other data in the graphs 512 may be determined in any other suitable manner or may be automatically controlled.

Figure 5D:
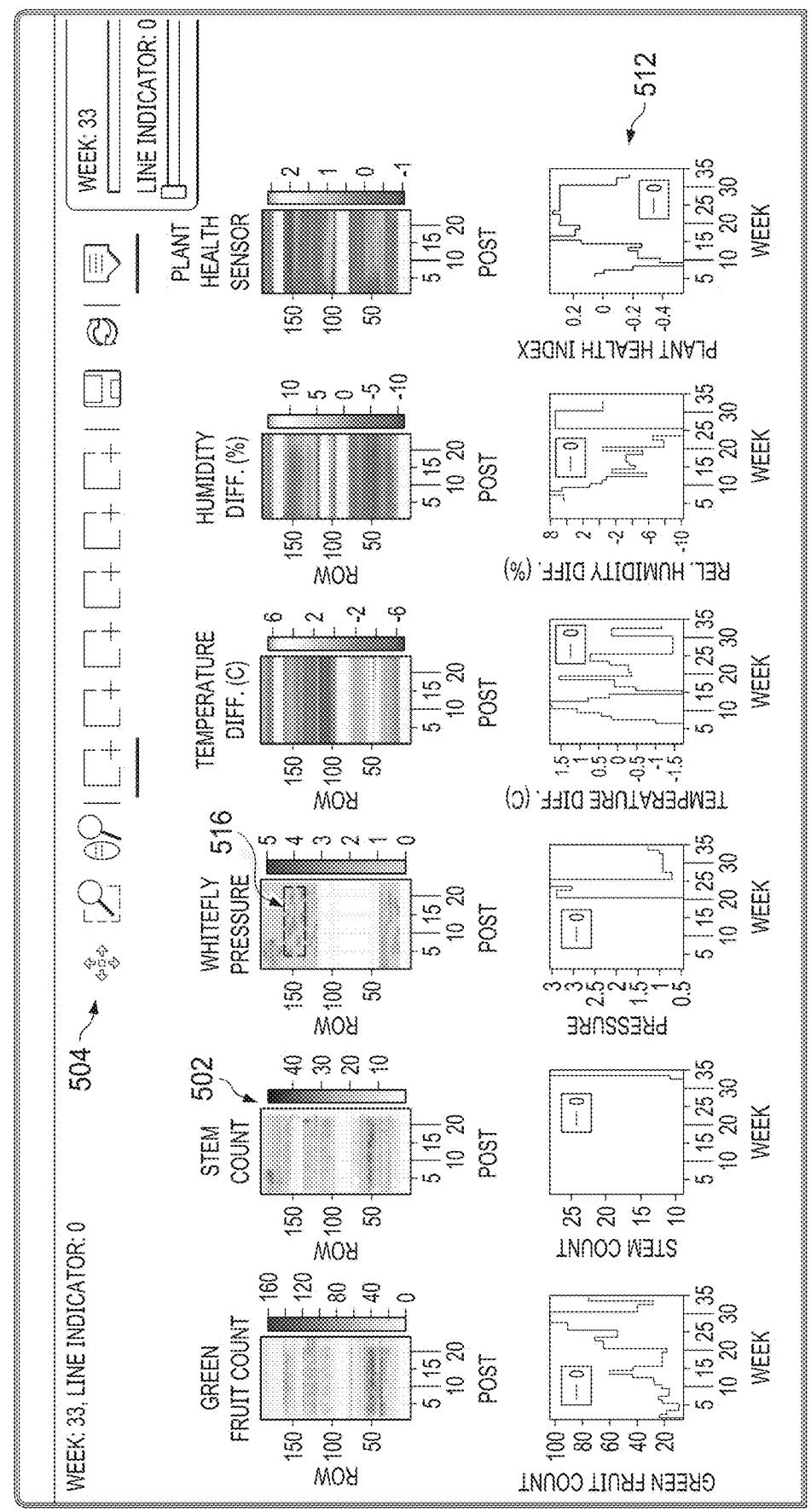

As shown in FIG. 5D, a user may select another one of the controls 504 and identify a selected area 516 in another one of the spatial maps 502. Again, the selected area 516 of the spatial map 502 corresponds to a selected portion of the growing area 104a-104n, and the graphs 512 are now updated with different lines associated with the selected area 516 of the spatial map 502. As can be seen here, the user may not be limited to selecting one or more areas in one of the spatial maps 502 and may instead be allowed to select any area or areas of interest in any of the spatial maps 502.

The various areas 510, 514, 516 within the visualization 500 may be selected in any suitable manner. For example, a user viewing the visualization 500 may use a stylus or otherwise provide input identifying one or more selected portions of displayed data in the visualization 500. This may allow the user to select data in order to see whether certain variables might have an effect on plant production or other plant-related characteristic. The data processing platform 102 may also automatically select one or more portions of the displayed data in the visualization 500. For instance, the data processing platform 102 may select portions of the displayed data in the visualization 500 that are most indicative of anomalies associated with the plants 106 in the growing area 104a-104n. The anomalies may be identified based on what appear to be significant (or at least statistically significant) differences in at least one plant-related characteristic across various plants 106 in the growing area 104a-104n.

Although FIG. 4 and FIGS. 5A through 5D illustrate examples of visualizations 400, 500 used for real-time identification of spatial production anomalies in agriculture, various changes may be made to FIGS. 4 and 5A through 5D. For example, the contents of the visualizations 400, 500 shown here are for illustration only and can vary widely based on collected data. Also, visualizations can come in a wide variety of forms, and FIGS. 4 and 5A through 5D do not limit this disclosure to any particular type of visualization. Further, any suitable controls may be used here to initiate functions associated with a visualization. In addition, the use of spatial maps as a mechanism for presenting plant-related information spatially is for illustration only, and plant-related information may be presented spatially or non-spatially in any other graphical or non-graphical format. For instance, audio information (such as in the form of an automated one-way or two-way voice-interaction system) may be used to provide spatially-relevant, spatially-based, or other information to one or more users from a cart 111, electronic device 112, or other device. This may allow, for example, a voice suggestion to be provided to at least one human scout 110 or other person as the person moves through one or more growing areas 104a-104n, such as to help guide at least one task or other work being performed by that person. Another mechanism for visually presenting information may be an augmented reality (AR) or mixed reality (MR) headset, an example of which is described below.

Figure 6:
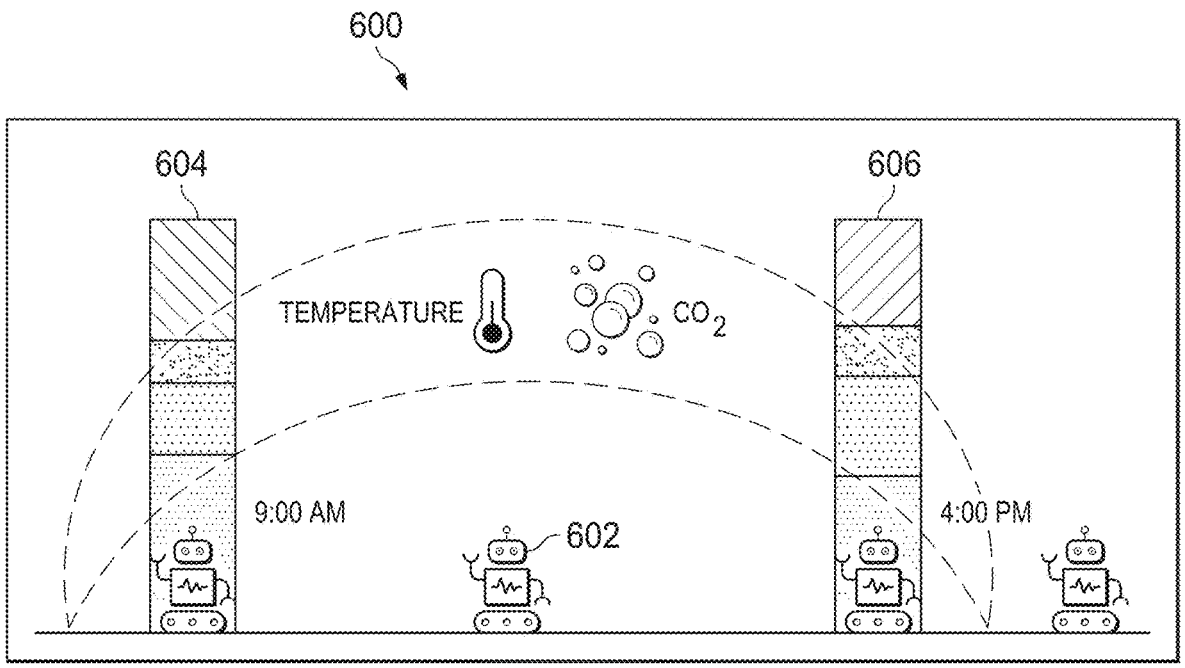
FIG. 6 illustrates example "time of day" variations that can affect spatially-distributed sensor measurements according to this disclosure.

FIG. 6 illustrates example "time of day" variations that can affect spatially-distributed sensor measurements according to this disclosure. More specifically, FIG. 6 illustrates an example environment 600 in which time of day variations can affect spatially-distributed sensor measurements. As noted above, plants 106 in one or more growing areas 104a-104n can be inspected by human scouts 110 or robotic scouts 114, but the plants 106 are spatially distributed in the growing area(s) 104a-104n. It is extremely unlikely that all plants 106 are constantly inspected at the same time of day. As a result, measurements associated with the plants 106 may experience time of day variations.

As shown in FIG. 6, a scout 602 (in this example a robotic scout) may be operating in a first location at a certain time of day and in a second location at a later time of day. A collection 604 of measurements captured at the first location (and associated with a first set of plants 106) and a collection 606 of measurements captured at the second location (and associated with a second set of plants 106) are also shown here. It is natural for certain measurements to vary based on the time of day, and this can make it extremely difficult if not impossible to make meaningful correlations or perform other operations based on these naturally-varying measurements. For example, it may not be possible to identify how temperatures, carbon dioxide levels, or other variables affect plant production accurately if the variables for different plants 106 are measured at different times of day.

The following description describes how measurements may be processed (such as during the pre-processing in step 306 of the method 300) in order to at least partially remove the effects of time of day variations from at least some of measurements. While some residual effects from time of day variations might still remain after processing of the measurements as discussed below, the results will suffer from significantly less time of day variations. As a result, this allows more accurate operations to occur using the measurements. For instance, this may allow a more direct comparison of various characteristics and measurements associated with the plants 106 in order to identify anomalies or to identify optimal growing and environmental conditions for the plants 106.

Although FIG. 6 illustrates one example of "time of day" variations that can affect spatially-distributed sensor measurements, various changes may be made to FIG. 6. For example, any number(s) and type(s) of measurements may be subject to time of day variations. Also, measurements captured by human scouts 110 or other data sources 118 may also be subject to time of day variations and may be processed as described below to at least partially reduce the time of day variations.

Figure 7:
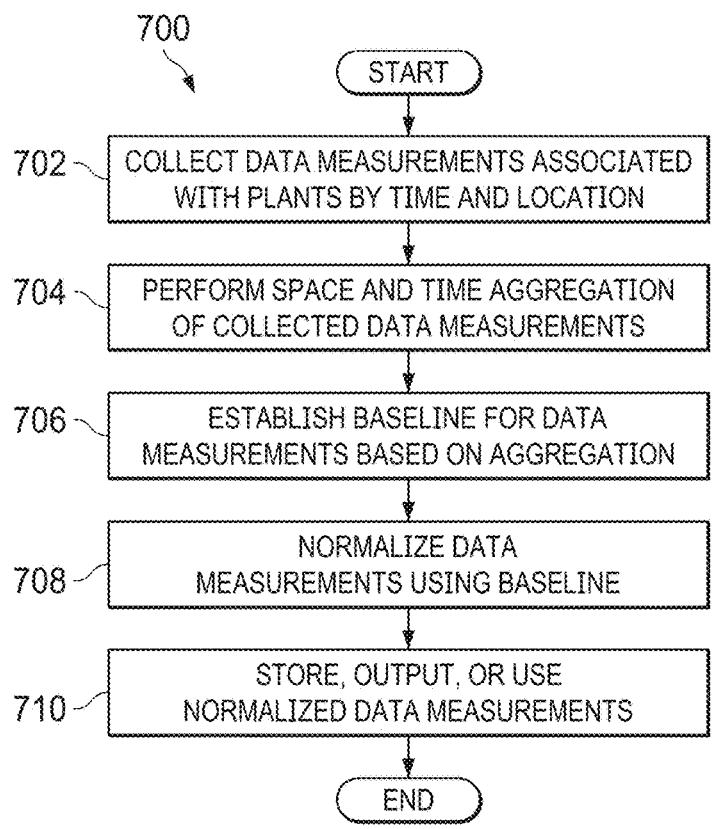
FIG. 7 illustrates an example method for normalizing spatially-distributed sensor measurements that suffer from "time of day" variations according to this disclosure.

FIG. 7 illustrates an example method 700 for normalizing spatially-distributed sensor measurements that suffer from "time of day" variations according to this disclosure. For ease of explanation, the method 700 is described as being performed using the system 100 of FIG. 1, including the data processing platform 102 (which may be implemented using the device 200 of FIG. 2). However, the method 700 may be performed using any suitable device(s) in any suitable system(s).

As shown in FIG. 7, data measurements associated with plants in at least one growing area are collected by time and location at step 702. This may include, for example, one or more human scouts 110 and/or one or more robotic scouts 114 recording or capturing data measurements associated with the plants 106 in at least one of the growing areas 104a-104n or with the at least one growing area 104a-104n. This may also include one or more other data sources 118 recording or capturing data measurements related to the plants 106 in at least one of the growing areas 104a-104n or related to at least one of the growing areas 104a-104n. The captured data measurements here relate to a specific characteristic that is associated with the plants 106, such as a particular climate-related characteristic or other characteristic. At least some of the data measurements are associated with times when the data measurements were captured and locations at which the data measurements were captured, such as row/post numbers, GPS coordinates, or other location information. Note that various data measurements may also be derived by the data processing platform 102 based on data received from the human scouts 110, robotic scouts 114, other data sources 118, or other sources. This may occur, for instance, when the data processing platform 102 applies at least one machine learning algorithm or other algorithm to images or other data obtained by the data processing platform 102.

The data measurements are aggregated by space and time at step 704. This may include, for example, the data processing platform 102 summing the data measurements, which are related to the same plant-related characteristic (such as temperature or carbon dioxide level) for all locations of the growing area(s) during each of multiple periods of time. As a particular example, the data processing platform 102 may sum all temperature measurements, carbon dioxide measurements, or other measurements for a specific characteristic captured for the growing area(s) 104a-104n in five-minute windows throughout each day. If data for a single day is being aggregated, this may involve summing all of the related data measurements within a moving or sliding five-minute window that were captured during that day. If data for multiple days is being aggregated, this may involve summing all of the related data measurements within a moving or sliding five-minute window that were captured across the multiple days, meaning the window would be used to sum the measurements captured at or around the same time for all of the days. In either case, the window is used so that data captured at or near the same time during the one or more days is summed together, and the window slides or is otherwise moved so that this can be repeated for different times of day. Note that windows of other lengths may be used, data may be aggregated over any desired number of days, and data may be summed in overlapping or non-overlapping time windows. As a particular example, data for a prior week or prior month may be aggregated and used here to form the baseline. The aggregation gives some indication of how the magnitudes of the overall measurements for the specific plant-related characteristic can vary during the day.

The aggregation is used to produce a baseline for the data measurements at step 706. This may include, for example, the data processing platform 102 smoothing or otherwise filtering the aggregation of the data measurements to produce a baseline for those data measurements. The baseline may be expressed in any suitable manner, such as a temperature, carbon dioxide level, or other measurement value that varies over the time of day. In other words, the baseline may identify, for any given time of day, a temperature, carbon dioxide level, or other measurement value that is based on the aggregation.

The data measurements are normalized based on the baseline at step 708. This may include, for example, the data processing platform 102 subtracting the baseline value for a particular time of day from the actual data measurements that were captured during that time of day. Note that while subtraction is used here in this example, other mechanisms (such as scaling or other normalization technique) based on the baseline may be used. The overall effect here is to reduce the impact of time of day variations in climate data or other data, which allows more effective comparisons of climate variables at different locations of one or more growing areas 104a-104n (even if those locations are scouted at different times of day).

The normalized data measurements are stored, output, or used in some manner at step 710. This may include, for example, using the normalized data measurements in the method 300 described above to perform real-time identification and resolution of spatial production anomalies in agriculture. This may also or alternatively include using the normalized data measurements as discussed below to identify improved or optimal growing and environmental conditions for at least one plant genotype or phenotype. As a particular example, this may include using the normalized data measurements to produce at least one visualization that includes or is based on the normalized data measurements. The normalized data measurements may be used in any other suitable manner.

Data measurements from a single growing area 104a-104n may be aggregated here and used to form at least one baseline for the growing area 104a-104n. Data measurements from multiple growing areas 104a-104n may also be aggregated here and used to form at least one baseline for the multiple growing areas 104a-104n. This may allow, for example, data for multiple growing areas 104a-104n at or near the same geographical location to be aggregated, since these growing areas 104a-104n would be expected to have similar climatic conditions or other time-of-day conditions (although in some instances that might not be the case). In general, one or more baselines may be identified here using data from one or more growing areas 104a-104n.

Although FIG. 7 illustrates one example of a method 700 for normalizing spatially-distributed sensor measurements that suffer from "time of day" variations, various changes may be made to FIG. 7. For example, while shown as a series of steps, various steps in FIG. 7 may overlap, occur in parallel, occur in a different order, or occur any number of times. As a particular example, the description above has assumed that measurement data for a single characteristic is being obtained and normalized. However, the same or similar approach can easily be used to normalize measurement data for any number of plant-related characteristics. Also, it is possible that the baseline produced using some data measurements is also or alternatively used to normalize other data measurements, such as when prior data measurements are used to determine a baseline for normalizing later-collected data measurements.

Figure 8:
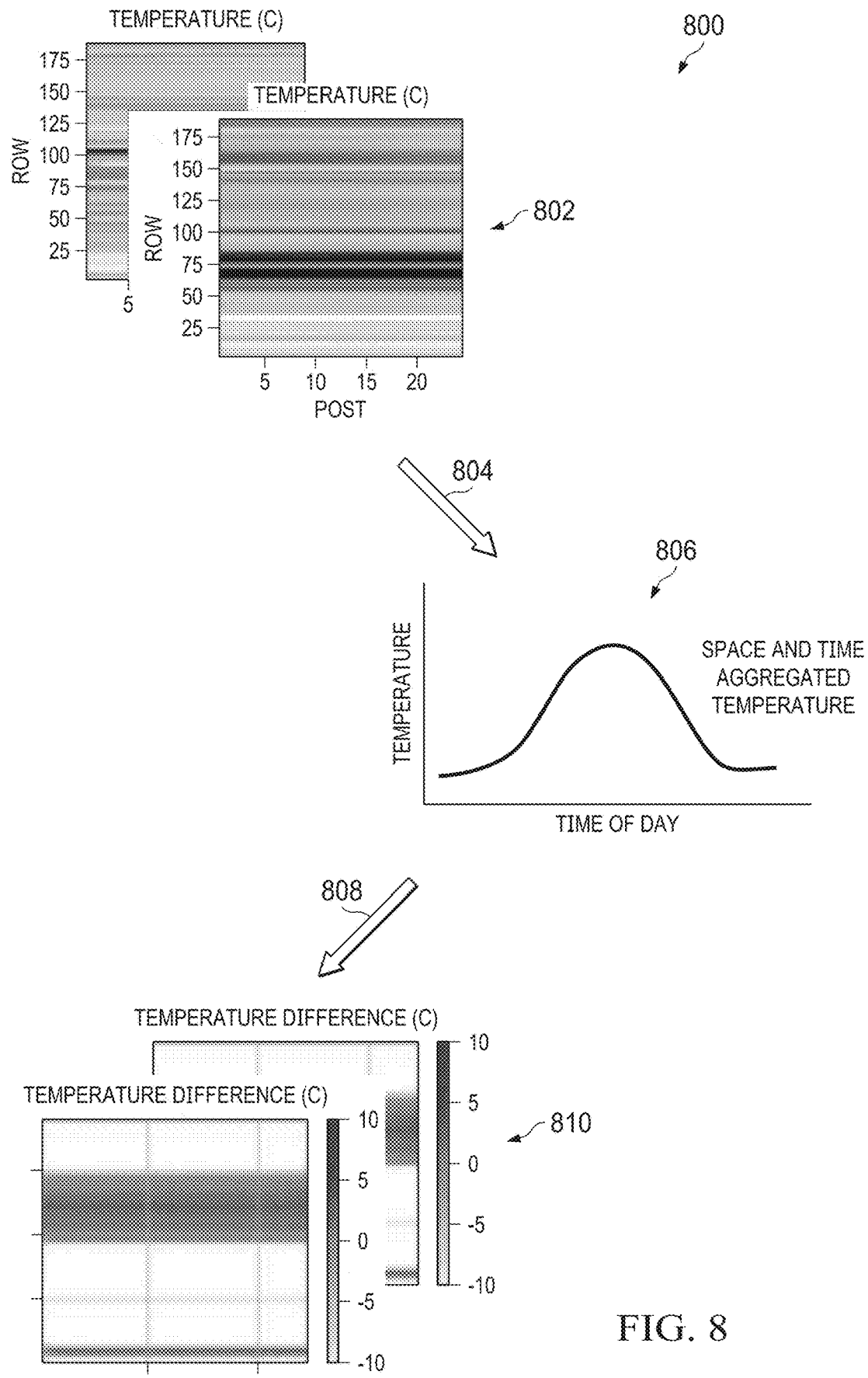
FIG. 8 illustrates an example process flow for normalizing spatially-distributed sensor measurements that suffer from "time of day" variations according to this disclosure.

FIG. 8 illustrates an example process flow 800 for normalizing spatially-distributed sensor measurements that suffer from "time of day" variations according to this disclosure. More specifically, the process flow 800 here represents how at least some of the steps from the method 700 of FIG. 7 may be performed and how data may flow during these steps.

As shown in FIG. 8, a collection 802 of data measurements has been obtained, which may occur during step 702 of the method 700. In this example, the data measurements are temperature measurements from or related to at least one specific growing area 104a-104n, although other types of data measurements may be obtained here. For instance, data measurements related to one or more of the climate data described above may be obtained here.

An aggregation operation 804 is applied to the collection 802 of data measurements in order to produce a baseline 806, which may occur during steps 704 and 706 of the method 700. For example, values of the data measurements in the collection 802 of data measurements within a moving or sliding time window can be summed, such as by summing the values of the measurement data captured within a moving or sliding five-minute window or window of other length. As discussed above, if data for a single day is being aggregated, all of the related data measurements in the collection 802 within the moving or sliding window may be summed. If data for multiple days is being aggregated, all of the related data measurements in the collection 802 across all of the days within the moving or sliding window can be summed. In either case, the window is used so that data captured at or near the same time during the one or more days is summed together, and the window slides or is otherwise moved so that this can be repeated for different times of day. Smoothing, filtering, or other processing operations may be performed on the original or aggregated data to produce the baseline 806. The baseline 806 here is expressed as an expected variation in the temperature measurements (or other measurements) as a function of the day.

A normalization operation 808 is applied to the collection 802 of data measurements using the baseline 806 in order to produce a collection 810 of normalized data measurements, which may occur during step 708 of the method 700. For example, the value identified by the baseline 806 for each particular time of day may be subtracted from any of the data measurements in the collection 802 of data measurements captured at or near that particular time of day. As noted above, operations other than subtraction (such as scaling) may also or alternatively occur during the normalization operation 808.

The normalized data measurements in the collection 810 represent relative measurements. The original data measurements in the collection 802 have been modified to at least partially remove time of day variations, and the resulting normalized data measurements in the collection 810 represent measurements of how the original data measurements in the collection 802 differ from the values in the baseline 806. That is why the normalized data measurements in the collection 810 are referred to as temperature "difference" values. As can be seen in FIG. 4, the same approach may be used to calculate various difference values, such as temperature difference values, humidity difference values, carbon dioxide difference values, and photosynthetically-active radiation difference values or other illumination difference values.

Although FIG. 8 illustrates one example of a process flow 800 for normalizing spatially-distributed sensor measurements that suffer from "time of day" variations, various changes may be made to FIG. 8. For example, the process flow 800 may be used to reduce or eliminate time of day variations from any suitable plant-related data measurements. Also, it is possible that the baseline 806 produced using data measurements in the collection 802 is also or alternatively used to normalize other data measurements, such as when prior data measurements are used to determine a baseline for normalizing later-collected data measurements.

Figure 9:
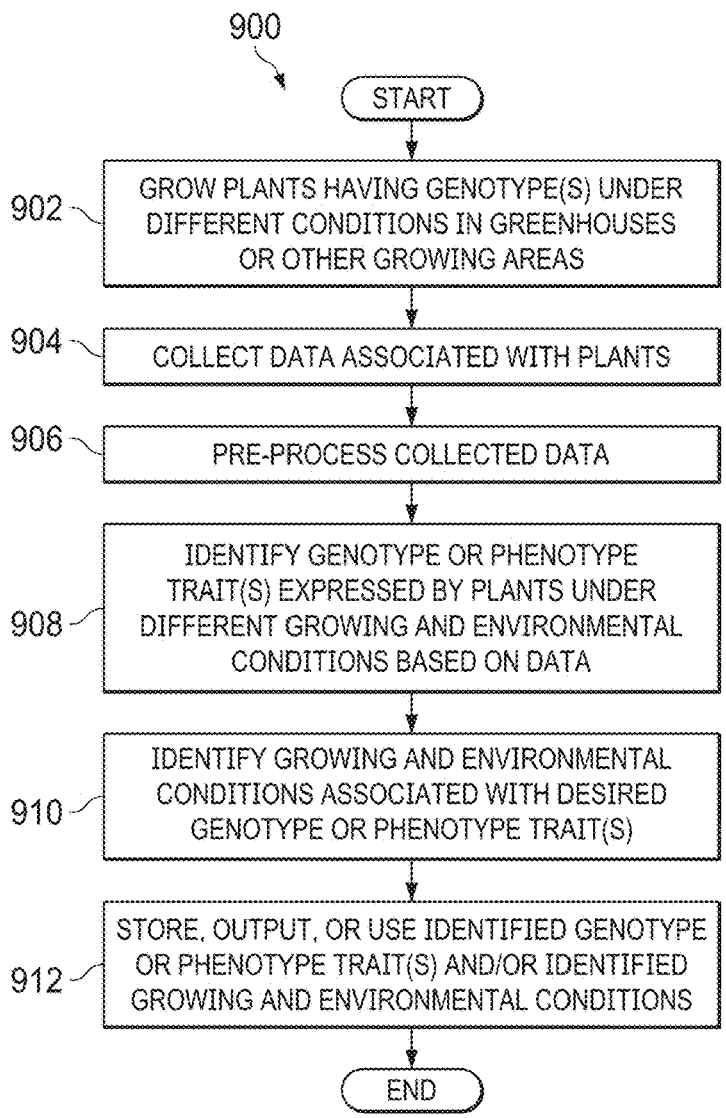
FIG. 9 illustrates an example method for using real-time identification of spatial production anomalies in agriculture according to this disclosure.

FIG. 9 illustrates an example method 900 for using real-time identification of spatial production anomalies in agriculture according to this disclosure. For ease of explanation, the method 900 is described as being performed using the system 100 of FIG. 1, including the data processing platform 102 (which may be implemented using the device 200 of FIG. 2). However, the method 900 may be performed using any suitable device(s) in any suitable system(s).

As noted above, the genotype of a plant seed, cutting, or tissue culture material is based on the specific genes carried in the seed, cutting, or tissue culture material. The phenotype of a plant refers to the characteristics of the plant that are actually expressed physically when the plant is growing. The phenotype of a plant is based on its genotype and its growing and environmental conditions, such as its climate, nutrients, pests, diseases, treatments, and crop work. For example, plant seeds, cuttings, or tissue culture materials that are bred or otherwise created to try and achieve at least one desired characteristic (such as the size or taste of fruits/vegetables or the size or color of ornamental flowers) may need certain climatic conditions or other growing and environmental conditions in order for the desired characteristic(s) of the plants to be expressed when the plants are actually growing. The method 900 shown here can be used (among other things) to help identify the growing and environmental condition or conditions under which one or more desired phenotypes of plants are expressed.

As shown in FIG. 9, multiple plants having at least one genotype are grown under different growing and environmental conditions in one or more greenhouses or other growing areas at step 902. This may include, for example, one or more growers growing various plants 106 (and possibly a very large number of plants 106) under different climatic conditions, watering conditions, nutrient conditions, or other conditions. This may also include the one or more growers applying different treatments to the plants 106 in order to treat different pests, diseases, or other conditions (note that the pests, diseases, or other conditions may not actually need to be present in order to test how the different treatments affect the plants 106). This may further include the one or more growers performing different types or amounts of crop work to the plants 106. In some cases, this step may involve numerous plants 106 being subjected to a large number of varying conditions.

Data measurements associated with the plants being grown under the various growing and environmental conditions are collected at step 904. This may include, for example, one or more human scouts 110 and/or one or more robotic scouts 114 recording or capturing data measurements associated with the various plants 106 or with the one or more growing areas 104a-104n and providing the data measurements to the data processing platform 102. This may also include one or more other data sources 118 recording or capturing data measurements related to the plants 106 or related to the one or more growing areas 104a-104n and providing the data measurements to the data processing platform 102. The captured data measurements here relate to a number of specific characteristics that are associated with the growing and environmental conditions of the plants 106. At least some of the data measurements are associated with locations at which the data measurements were captured, such as row/post numbers, GPS coordinates, or other location information, which allows the data measurements to be associated with specific plants 106. Note that various data measurements may also be derived by the data processing platform 102 based on data received from the human scouts 110, robotic scouts 114, other data sources 118, or other sources. This may occur, for instance, when the data processing platform 102 applies at least one machine learning algorithm or other algorithm to images or other data obtained by the data processing platform 102.

The data measurements may be pre-processed at step 906. This may include, for example, the data processing platform 102 filtering the collected data and removing bad or invalid data. This may also include the data processing platform 102 performing the technique described above with respect to FIGS. 7 and 8 to at least partially remove time of day variations from at least some of the collected data.

The data may be processed to identify any desired information about the plants 106 being grown. For example, the actual genotype or phenotype trait(s) expressed by the plants while being grown under the different growing and environmental conditions can be identified at step 908. This may include, for example, the data processing platform 102 identifying one or more characteristics of the plants 106 that were actually expressed by the plants 106 during their growth based on the collected data. The one or more characteristics of the plants 106 may relate to fruits, vegetables, ornamental flowers, or other production items produced by the plants 106 or to other characteristics of the plants 106. As a particular example, this may include the data processing platform 102 identifying how the sizes, quantities, or qualities of fruits, vegetables, flowers, or other production produced by the plants 106 varied under the different growing and environmental conditions. As another example, one or more growing or environmental conditions associated with at least one desired genotype or phenotype trait of the plants can be identified at step 910. This may include, for example, the data processing platform 102 identifying one or more growing or environmental conditions associated with a desired plant production or other desired characteristic(s) of the plants 106.

The results of the processing are stored, output, or used in some manner at step 912. This may include, for example, the data processing platform 102 outputting growing and environmental conditions that have been identified as being possible growing and environmental conditions in order to achieve one or more specific genotype or phenotype traits. The processing results here may be used for any suitable purpose(s), such as to provide plant breeders with information that can be shared with customers (such as in the form of growing advice for growers) or to provide plant breeders with information that can be used to provide production guarantees to customers. In general, this approach allows consideration of the genotypes of seeds, cuttings, or tissue culture materials as a contributor to plant production or other plant characteristics (along with the growing and environmental conditions), and the results may be used in any suitable manner.

Although FIG. 9 illustrates one example of a method 900 for using real-time identification of spatial production anomalies in agriculture, various changes may be made to FIG. 9. For example, while shown as a series of steps, various steps in FIG. 9 may overlap, occur in parallel, occur in a different order, or occur any number of times. As a particular example, plants 106 may be grown in step 902 and data associated with those plants 106 may be collected in step 904 over multiple growing seasons. This may be done, for instance, in order to obtain a desired amount of data or a desired amount of variability in the growing and environmental conditions. In some cases, the data collected during one growing season or for some plants 106 may be used to identify how growing and environmental conditions might be set or altered during another growing season or for other plants 106.

Figure 10:
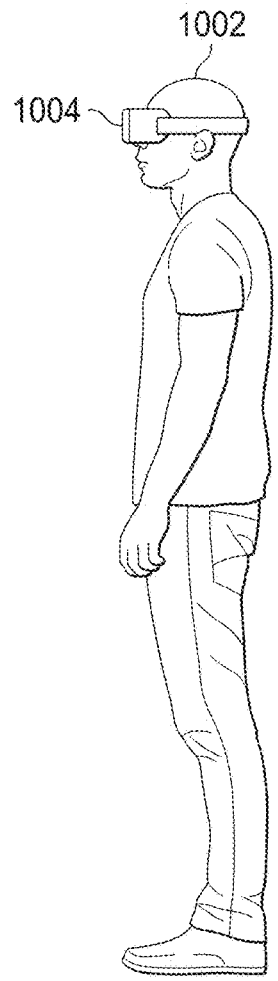
FIG. 10 illustrates an example of a wearable device for use in presenting information related to spatial production anomalies or other plant-related information according to this disclosure.

FIG. 10 illustrates an example of a wearable device for use in presenting information related to spatial production anomalies or other plant-related information according to this disclosure. As shown in FIG. 10, a user 1002 is wearing an AR or MR headset 1004. The headset 1004 is configured to generate and display AR- or MR-related information to the user 1002. Often times, this may typically involve displaying one or more AR or MR objects or other AR- or MR-related information over or within a physical scene being viewed by the user 1002. Each AR or MR object may represent an artificially-created object that the user 1002 is able to view and optionally interact with virtually.

The headset 1004 may be used in a number of ways to facilitate interactions with the user 1002. For example, the headset 1004 may be used to present one or more visualizations, such as the visualizations 400 and 500, to the user 1002. If the visualization 500 is presented, the headset 1004 may also allow the user 1002 to select one or more areas (such as the areas 510, 514, 516) within the visualization 500 in order to view the graphs 512.

As another example, the headset 1004 may be worn by the user 1002, such as a human scout 110 or other person, as the user 1002 moves through one or more growing areas 104a-104n. The headset 1004 may be used to present spatially-relevant information or other information to the user 1002 related to the one or more growing areas 104a-104n. For instance, the headset 1004 may be used to identify a specific plant 1006 or a specific group of plants 106 in a growing area and one or more actions to be performed involving the plant(s) 106. If the user 1002 is farther away from the one or more plants 106, the headset 1004 may provide information (such as in the form of arrows or other indicators) identifying where the user 1002 should travel in order to reach the plant(s) 106. The headset 1004 may also or alternatively be used to help guide at least one task or other work being performed by the user 1002.

The information that is presented to the user 1002 via the headset 1004 may come from any suitable source(s), such as the data processing platform 102. The data processing platform 102 may also track the location of the user 1002 via the headset 1004 or other mechanism in order to select which information should be provided to the user 1002 via the headset 1004. For instance, the data processing platform 102 may identify the user 1002 using the headset 1004 and identify various tasks to be performed by the user 1002. The data processing platform 102 can then provide information to the headset 1004, where the information relates to each task to be performed by the user 1002.

The headset 1004 may also be used to capture information about how one or more tasks are being performed by the user 1002 and to provide that information to the data processing platform 102. For example, the headset 1004 may capture information identifying how the user 1002 is performing crop work or implementing treatments involving the plants 106. The captured information may be provided to the data processing platform 102, where this information may be used to form at least part of the crop work data or the crop treatment data, respectively.

Although FIG. 10 illustrates one example of a wearable device for use in presenting information related to spatial production anomalies or other plant-related information, various changes may be made to FIG. 10. For example, the headset 1004 may have any suitable form, and this disclosure is not limited to use with any particular type of headset. Also, any other suitable wearable devices may be used here. In addition, the use of wearable devices is optional in the system 100 or other system.

In some embodiments, various functions described in this patent document are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive (HDD), a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable storage device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
at least one processor configured to:
obtain data measurements associated with plants in at least one growing area, the data measurements associated with one or more characteristics of the plants and one or more characteristics of the at least one growing area;
process at least some of the data measurements to identify one or more anomalous plant production issues associated with the plants, at least one of the one or more anomalous plant production issues associated with uneven production by the plants in at least part of the at least one growing area;
generate at least one visualization presenting at least some of the data measurements or processed versions of at least some of the data measurements in a spatial manner that corresponds to the at least one growing area, the at least one visualization identifying information associated with the one or more anomalous plant production issues and including a first visualization that includes a spatial map showing values of a specific characteristic of the plants in the at least one growing area and a second visualization displayed adjacent to the first visualization;
receive multiple selections of first graphical user interface elements displayed within multiple areas of the spatial map selecting the multiple areas of the spatial map from a user; and
in response to receiving the multiple selections of the first graphical user interface elements displayed within multiple areas of the spatial map selecting the multiple areas of the spatial map from the user:
generate second graphical user interface elements displayed within the spatial map identifying the selections of the multiple areas of the spatial map; and
populate third graphical user interface elements displayed within the second visualization with data associated with each of the multiple selected areas of the spatial map, wherein the data associated with each of the multiple selected areas of the spatial map is displayed simultaneously in the second visualization to permit comparison of different parts of the at least one growing area.

2. The apparatus of claim 1, wherein the at least one visualization further comprises a visualization that includes one or more spatial maps showing values of one or more variables affecting the specific characteristic of the plants in the at least one growing area.

3. The apparatus of claim 2, wherein:
the at least one visualization further includes multiple graphs associated with the specific characteristic of the plants in the at least one growing area and the one or more variables affecting the specific characteristic; and
contents of the graphs are based on at least one selected area within at least one of the spatial maps and include data plotted over time for the specific characteristic and the one or more variables within the at least one selected area.

4. The apparatus of claim 1, wherein the at least one visualization further comprises a visualization that includes:
spatial maps showing a time progression of values of a specific characteristic of the plants in the at least one growing area; and
spatial maps showing a time progression of values of one or more variables affecting the specific characteristic of the plants in the at least one growing area.

5. The apparatus of claim 1, wherein the at least one visualization further comprises one or more visualizations plotting at least some of the data measurements or one or more statistics based on at least some of the data measurements for at least part of the at least one growing area.

6. The apparatus of claim 1, wherein the at least one processor is configured to apply at least one machine learning algorithm in order to obtain at least some of the data measurements.

7. The apparatus of claim 6, wherein the at least one processor is configured to apply the at least one machine learning algorithm in order to generate at least one of:
data measurements comprising counts of production items produced by the plants;
data measurements comprising states of the production items produced by the plants;
data measurements comprising stem counts associated with the plants; and
data measurements comprising stem densities associated with the plants.

8. The apparatus of claim 1, wherein the at least one processor is further configured to generate one or more models associating at least one of the one or more characteristics of the plants and at least one of the one or more characteristics of the at least one growing area.

9. The apparatus of claim 8, wherein:
the one or more models comprise one or more predictive dynamic models; and
the at least one processor is further configured to predict how to make one or more adjustments to one or more growing or environmental conditions associated with the plants in order to at least partially reduce the uneven production by the plants.

10. The apparatus of claim 8, wherein the at least one processor is further configured to recommend or trigger one or more actions in order to reduce or eliminate the one or more anomalous plant production issues, the one or more actions based on at least one of the one or more models.

11. The apparatus of claim 10, wherein at least one of the one or more actions is spatially varying and affects different plants in different locations of the at least one growing area differently.

12. The apparatus of claim 10, wherein the at least one processor is further configured to:
monitor a reaction of one or more of the plants to performance of the one or more actions; and
determine whether to continue with the one or more actions, cease the one or more actions, or perform one or more other or additional actions based on whether a desired result has been obtained with the one or more plants.

13. The apparatus of claim 10, wherein the one or more actions comprise at least one of:
one or more actions performed by at least one human; and
one or more actions performed automatically.

14. The apparatus of claim 1, wherein the at least one processor is further configured to at least partially remove time of day variations from at least some of the data measurements.

15. The apparatus of claim 1, wherein the data measurements comprise:
plant production data measurements associated with one or more characteristics of production items produced by the plants;
physical plant data measurements associated with one or more physical characteristics of the plants;
climate data measurements associated with one or more climatic conditions affecting the plants;
pest and disease data measurements associated with one or more pests or diseases affecting the plants;
crop work data measurements associated with one or more characteristics of how humans or machines manipulate and modify the plants; and
crop treatment data measurements associated with one or more treatments applied to at least some of the plants.

16. The apparatus of claim 1, wherein the at least one processor is configured to obtain at least some of the data measurements from at least one of:
one or more electronic devices used by one or more human scouts; and
one or more robotic scouts.

17. The apparatus of claim 1, wherein the at least one processor forms a part of a cloud-based platform.

18. The apparatus of claim 1, wherein the at least one processor is further configured to provide the at least one visualization or other plant-related information to at least one wearable device associated with the user.

19. A non-transitory computer readable medium containing instructions that when executed cause at least one processor to:
obtain data measurements associated with plants in at least one growing area, the data measurements associated with one or more characteristics of the plants and one or more characteristics of the at least one growing area;
process at least some of the data measurements to identify one or more anomalous plant production issues associated with the plants, at least one of the one or more anomalous plant production issues associated with uneven production by the plants in at least part of the at least one growing area;
generate at least one visualization presenting at least some of the data measurements or processed versions of at least some of the data measurements in a spatial manner that corresponds to the at least one growing area, the at least one visualization identifying information associated with the one or more anomalous plant production issues and including a first visualization that includes a spatial map showing values of a specific characteristic of the plants in the at least one growing area and a second visualization displayed adjacent to the first visualization;
receive multiple selections of first graphical user interface elements displayed within multiple areas of the spatial map selecting the multiple areas of the spatial map from a user; and
in response to receiving the multiple selections of the first graphical user interface elements displayed within multiple areas of the spatial map selecting the multiple areas of the spatial map from the user:
generate second graphical user interface elements displayed within the spatial map identifying the selections of the multiple areas of the spatial map; and
populate third graphical user interface elements displayed within the second visualization with data associated with each of the multiple selected areas of the spatial map, wherein the data associated with each of the multiple selected areas of the spatial map is displayed simultaneously in the second visualization to permit comparison of different parts of the at least one growing area.

20. The non-transitory computer readable medium of claim 19, wherein the at least one visualization further comprises a visualization that includes one or more spatial maps showing values of one or more variables affecting the specific characteristic of the plants in the at least one growing area.

21. The non-transitory computer readable medium of claim 20, wherein:
the at least one visualization further includes multiple graphs associated with the specific characteristic of the plants in the at least one growing area and the one or more variables affecting the specific characteristic; and
contents of the graphs are based on at least one selected area within at least one of the spatial maps and include data plotted over time for the specific characteristic and the one or more variables within the at least one selected area.

22. The non-transitory computer readable medium of claim 19, wherein the at least one visualization further comprises a visualization that includes:
spatial maps showing a time progression of values of a specific characteristic of the plants in the at least one growing area; and
spatial maps showing a time progression of values of one or more variables affecting the specific characteristic of the plants in the at least one growing area.

23. The non-transitory computer readable medium of claim 19, wherein the at least one visualization further comprises one or more visualizations plotting at least some of the data measurements or one or more statistics based on at least some of the data measurements for at least part of the at least one growing area.

24. The non-transitory computer readable medium of claim 19, further containing instructions that when executed cause the at least one processor to:
apply at least one machine learning algorithm in order to obtain at least some of the data measurements.

25. The non-transitory computer readable medium of claim 24, wherein the at least one machine learning algorithm is configured to generate at least one of:
data measurements comprising counts of production items produced by the plants;
data measurements comprising states of the production items produced by the plants;
data measurements comprising stem counts associated with the plants; and
data measurements comprising stem densities associated with the plants.

26. The non-transitory computer readable medium of claim 19, further containing instructions that when executed cause the at least one processor to:
generate one or more models associating at least one of the one or more characteristics of the plants and at least one of the one or more characteristics of the at least one growing area.

27. The non-transitory computer readable medium of claim 26, wherein:
the one or more models comprise one or more predictive dynamic models; and
further containing instructions that when executed cause the at least one processor to: predict how to make one or more adjustments to one or more growing or environmental conditions associated with the plants in order to at least partially reduce the uneven production by the plants.

28. The non-transitory computer readable medium of claim 26, further containing instructions that when executed cause the at least one processor to:
recommend or trigger one or more actions in order to reduce or eliminate the one or more anomalous plant production issues, the one or more actions based on at least one of the one or more models.

29. The non-transitory computer readable medium of claim 28, wherein at least one of the one or more actions is spatially-varying and affects different plants in different locations of the at least one growing area differently.

30. The non-transitory computer readable medium of claim 28, further containing instructions that when executed cause the at least one processor to:
monitor a reaction of one or more of the plants to performance of the one or more actions; and
determine whether to continue with the one or more actions, cease the one or more actions, or perform one or more other or additional actions based on whether a desired result has been obtained with the one or more plants.

31. The non-transitory computer readable medium of claim 28, wherein the one or more actions comprise at least one of:
one or more actions performed by at least one human; and
one or more actions performed automatically.

32. The non-transitory computer readable medium of claim 19, further containing instructions that when executed cause the at least one processor to:
at least partially remove time of day variations from at least some of the data measurements.

33. The non-transitory computer readable medium of claim 19, wherein the data measurements comprise:
plant production data measurements associated with one or more characteristics of production items produced by the plants;
physical plant data measurements associated with one or more physical characteristics of the plants;
climate data measurements associated with one or more climatic conditions affecting the plants;
pest and disease data measurements associated with one or more pests or diseases affecting the plants;
crop work data measurements associated with one or more characteristics of how humans or machines manipulate and modify the plants; and
crop treatment data measurements associated with one or more treatments applied to at least some of the plants.

34. The non-transitory computer readable medium of claim 19, wherein the instructions that when executed cause the at least one processor to obtain the data measurements comprise:
instructions that when executed cause the at least one processor to obtain at least some of the data measurements from at least one of:
one or more electronic devices used by one or more human scouts; and
one or more robotic scouts.

35. The non-transitory computer readable medium of claim 19, further containing instructions that when executed cause the at least one processor to:
provide the at least one visualization or other plant-related information to at least one wearable device associated with at least one user.

36. A method comprising:
obtaining data measurements associated with plants in at least one growing area, the data measurements associated with one or more characteristics of the plants and one or more characteristics of the at least one growing area;
processing at least some of the data measurements to identify one or more anomalous plant production issues associated with the plants, at least one of the one or more anomalous plant production issues associated with uneven production by the plants in at least part of the at least one growing area; and
generating at least one visualization presenting at least some of the data measurements or processed versions of at least some of the data measurements in a spatial manner that corresponds to the at least one growing area, the at least one visualization identifying information associated with the one or more anomalous plant production issues and including a first visualization that includes a spatial map showing values of a specific characteristic of the plants in the at least one growing area and a second visualization displayed adjacent to the first visualization;
receiving multiple selections of first graphical user interface elements displayed within multiple areas of the spatial map selecting the multiple areas of the spatial map from a user; and
in response to receiving the multiple selections of the first graphical user interface elements displayed within multiple areas of the spatial map selecting the multiple areas of the spatial map from the user:
generating second graphical user interface elements displayed within the spatial map identifying the selections of the multiple areas of the spatial map; and
populating third graphical user interface elements displayed within the second visualization with data associated with each of the multiple selected areas of the spatial map, wherein the data associated with each of the multiple selected areas of the spatial map is displayed simultaneously in the second visualization to permit comparison of different parts of the at least one growing area.

37. The method of claim 36, wherein the at least one visualization further comprises a visualization that includes one or more spatial maps showing values of one or more variables affecting the specific characteristic of the plants in the at least one growing area.

38. The method of claim 37, wherein:
the at least one visualization further includes multiple graphs associated with the specific characteristic of the plants in the at least one growing area and the one or more variables affecting the specific characteristic; and
contents of the graphs are based on at least one selected area within at least one of the spatial maps and include data plotted over time for the specific characteristic and the one or more variables within the at least one selected area.

39. The method of claim 36, wherein the at least one visualization further comprises a visualization that includes:
spatial maps showing a time progression of values of a specific characteristic of the plants in the at least one growing area; and
spatial maps showing a time progression of values of one or more variables affecting the specific characteristic of the plants in the at least one growing area.

40. The method of claim 36, wherein the at least one visualization further comprises one or more visualizations plotting at least some of the data measurements or one or more statistics based on at least some of the data measurements for at least part of the at least one growing area.

41. The method of claim 36, further comprising:
applying at least one machine learning algorithm in order to obtain at least some of the data measurements.

42. The method of claim 41, wherein applying the at least one machine learning algorithm comprises generating at least one of:
data measurements comprising counts of production items produced by the plants;
data measurements comprising states of the production items produced by the plants;
data measurements comprising stem counts associated with the plants; and
data measurements comprising stem densities associated with the plants.

43. The method of claim 36, further comprising:
generating one or more models associating at least one of the one or more characteristics of the plants and at least one of the one or more characteristics of the at least one growing area.

44. The method of claim 43, wherein:
the one or more models comprise one or more predictive dynamic models; and
the method further comprises predicting how to make one or more adjustments to one or more growing or environmental conditions associated with the plants in order to at least partially reduce the uneven production by the plants.

45. The method of claim 43, further comprising:
recommending or triggering one or more actions in order to reduce or eliminate the one or more anomalous plant production issues, the one or more actions based on at least one of the one or more models.

46. The method of claim 45, wherein at least one of the one or more actions is spatially-varying and affects different plants in different locations of the at least one growing area differently.

47. The method of claim 45, further comprising:
monitoring a reaction of one or more of the plants to performance of the one or more actions; and
determining whether to continue with the one or more actions, cease the one or more actions, or perform one or more other or additional actions based on whether a desired result has been obtained with the one or more plants.

48. The method of claim 45, wherein the one or more actions comprise at least one of:
one or more actions performed by at least one human; and
one or more actions performed automatically.

49. The method of claim 36, further comprising:
at least partially removing time of day variations from at least some of the data measurements.

50. The method of claim 36, wherein the data measurements comprise:
plant production data measurements associated with one or more characteristics of production items produced by the plants;
physical plant data measurements associated with one or more physical characteristics of the plants;
climate data measurements associated with one or more climatic conditions affecting the plants;
pest and disease data measurements associated with one or more pests or diseases affecting the plants;

crop work data measurements associated with one or more characteristics of how humans or machines manipulate and modify the plants; and crop treatment data measurements associated with one or more treatments applied to at least some of the plants.

51. The method of claim 36, wherein obtaining the data measurements comprises:

obtaining at least some of the data measurements from at least one of:

one or more electronic devices used by one or more human scouts; and one or more robotic scouts.

52. The method of claim 36, wherein processing at least some of the data measurements comprises processing at least some of the data measurements using a cloud-based platform.

53. The method of claim 36, further comprising:

providing the at least one visualization or other plant-related information to at least one wearable device associated with at least one user.

* * * * *